United States Patent [19]

Kitazawa et al.

[11] Patent Number: 5,145,869
[45] Date of Patent: Sep. 8, 1992

[54] PHENYLSULFONYLALKANOIC ACID COMPOUNDS AND PHARMACEUTICALS THEREOF

[75] Inventors: Makio Kitazawa; Masuo Akahane, both of Matsumoto; Yasushi Nakano, Shiojiri; Atsushi Tsubaki, Matsumoto; Kazuaki Sato, Matsumoto; Masaaki Ban, Matsumoto; Michihiro Kobayashi, Akashina, all of Japan

[73] Assignee: Kissei Pharmaceutical Co., Ltd., Japan

[21] Appl. No.: 683,247

[22] Filed: Apr. 11, 1991

[51] Int. Cl.$^5$ .............. A61K 31/215; C07C 317/14; C07C 321/28
[52] U.S. Cl. .................... 514/510; 514/538; 514/539; 514/562; 560/12; 560/17; 562/430; 562/431
[58] Field of Search .............. 562/430, 431; 560/12, 560/17; 514/510, 538, 539, 562

[56] References Cited

U.S. PATENT DOCUMENTS

| | | | |
|---|---|---|---|
| 4,948,810 | 8/1990 | Iwakuma et al. | 560/12 X |
| 5,002,967 | 3/1991 | Mueller et al. | 560/17 X |
| 5,006,542 | 4/1991 | Hall et al. | 560/12 |
| 5,008,434 | 4/1991 | Rossey et al. | 560/17 |

Primary Examiner—Jose G. Dees
Assistant Examiner—Vera C. Clarke
Attorney, Agent or Firm—Depaoli & O'Brien

[57] ABSTRACT

The present invention provides a novel class of phenylsulfonylalkanoic acid compounds such as a structure corresponding to the formula:

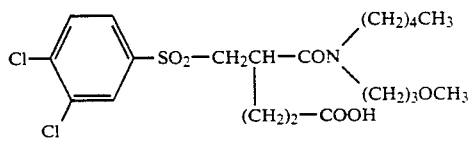

or a pharmaceutically acceptable salt thereof.

A present invention phenylsulfonylalkanoic acid compound is useful for prevention or treatment of irritable bowel syndrome, biliary dyskinesia and acute pancreatitis.

10 Claims, No Drawings

PHENYLSULFONYLALKANOIC ACID COMPOUNDS AND PHARMACEUTICALS THEREOF

FIELD OF THE INVENTION

The present invention relates to phenylsulfonylalkanoic acid compounds being useful for therapeutic agents.

More particularly, the present invention relates to novel phenylsulfonylalkanoic acid compounds represented by the formula:

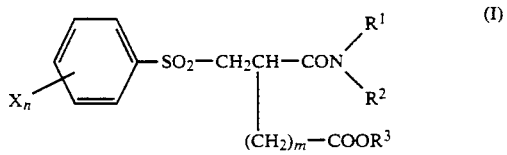

wherein $R^1$ represents an alkyl group having 1 to 10 carbon atoms, an alkoxyalkyl group having 3 to 7 carbon atoms or an aralkyl group having 7 to 12 carbon atoms; $R^2$ represents an alkyl group having 1 to 10 carbon atoms or an aralkyl group having 7 to 12 carbon atoms; $R^3$ represents a hydrogen atom or an alkyl group having 1 to 4 carbon atoms; X represents a halogen atom, an alkyl group having 1 to 3 carbon atoms, a nitro group or an acetyl group; m is an integer of from 1 to 3; n is 1 or 2; and pharmaceutically acceptable salts thereof.

BACKGROUND OF THE INVENTION

Cholecystokinin, hereinafter referred to as CCK, is a typical gastrointestinal hormone with activity that stimulates exocrine pancreatic secretion and contracts the gallbladder.

PRIOR ART

Analogs of Proglumide represented by the formula:

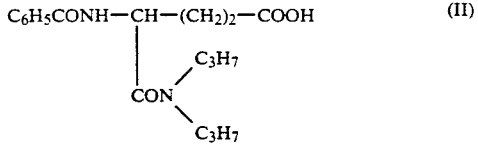

are reported in patent applications which include Japanese Patent Application (OPI) Nos. 44855/86, 181246/87, 27468/88, 165352/88 and 201156/88 (The term "OPI" used herein refers to an unexamined Japanese Patent Application), EP(A1)0308885, EP-(A2)0272228, WO87/03869, WO88/05774 and WO89/02431. The compounds described in these patent applications are derived from amino acid compounds such as glutamic acid or aspartic acid.

The present invention provides novel phenylsulfonylalkanoic acid compounds which exhibit strong antagonistic activities toward CCK receptors, and thus they are useful as therapeutic agents for the prevention and treatment of irritable bowel syndrome, biliary dyskinesia and acute pancreatitis.

SUMMARY OF THE INVENTION

An object of the present invention is to provide novel phenylsulfonylalkanoic acid compounds which exhibit a strong antagonistic activity toward CCK receptors.

A further object of the present invention is to provide pharmaceutical compositions containing a phenylsulfonylalkanoic acid compound as an active ingredient.

Other objects, features and advantages of the present invention will be apparent from the following description of the invention.

DETAILED DESCRIPTION OF THE INVENTION

The present invention provides phenylsulfonylalkanoic acid compounds which exhibit antagonistic activity toward CCK receptors.

The phenylsulfonylalkanoic acid compounds of the present invention competitively inhibit CCK-8 from binding to CCK receptors, and thus exhibit inhibitory activities against gallbladder contraction and amylase secretion by CCK-8.

Thus, the phenylsulfonylalkanoic acid compounds of the present invention are useful as therapeutic agents for the prevention or treatment of irritable bowel syndrome, biliary dyskinesia and acute pancreatitis.

The term "alkyl" in the present invention refers to a straight or branched alkyl group having 1 to 10 carbon atoms, such as methyl or isobutyl.

The term "alkoxyalkyl" in the present invention refers to a straight or branched alkoxyalkyl group having 3 to 7 carbon atoms, such as methoxyethyl or isopropoxyethyl.

The term "aralkyl" in the present invention refers to a straight or branched alkyl group having a phenyl substituent and having 7 to 12 carbon atoms, such as benzyl, phenethyl or phenylpropyl.

The novel phenylsulfonylalkanoic acid compounds of formula (I) can be prepared by oxidizing phenylthioalkanoic acid compounds represented by the formula:

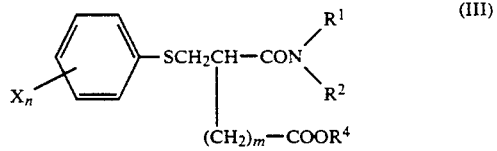

wherein $R^1$, $R^2$, X, m, and n are as previously defined; $R^4$ represents an alkyl group having 1 to 4 carbon atoms, or by oxidizing phenylsulfinylalkanoic acid compounds represented by the formula:

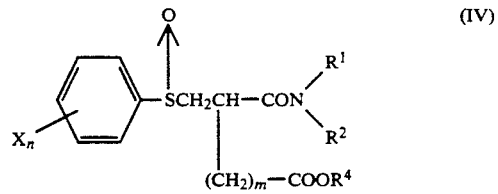

wherein $R^1$, $R^2$, $R^4$, X, m and n are as previously defined.

The corresponding carboxylic acid compounds can be prepared by hydrolysis of the ester products.

The present invention phenylsulfonylalkanoic acid formula (I) compounds have one asymmetric carbon atom in the structure, and consequently exist in the form of two optical isomers. The configuration of substituents on the asymmetric carbon atom is not limited, and S-configuration, R-configuration or a mixture of S- and R-configurations can be employed in the present invention.

Phenylsulfonylalkanoic acid formula (I) compounds in which $R^1$ is an alkyl group or an alkoxyalkyl group, $R^2$ is an alkyl group, $R^3$ is a hydrogen atom, X is a halogen atom, m is 2 and n is 2 are preferred structures in the practice of the present invention embodiments.

Particularly preferred invention phenylsulfonylalkanoic acid compounds include 5-(3,4-dichlorophenylsulfonyl)-4-[N-(3-methoxypropyl)-N-pentylcarbamoyl]pentanoic acid, its optical isomers and the pharmaceutically acceptable salts thereof.

The compounds of formula (III) used as starting materials in the present invention are novel compounds and can be prepared by reacting thiophenol compounds represented by the formula:

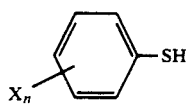
(V)

where X and n are as previously defined with compounds represented by the formula:

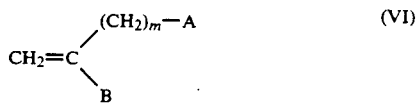
(VI)

where (1) A and B are the same and are a cyano group or an alkoxycarbonyl group having 2 to 5 carbon atoms, or (2) A represents an alkoxycarbonyl group having 2 to 5 carbon atoms and B represents a carboxy group or alkali metal salts thereof, and m is as previously defined, in the presence of a Lewis-base or Lewis-acid to form a product represented by the formula:

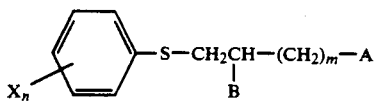
(VII)

wherein A, B, X, m, and n are as previously defined.

As a further alternative, hydrolyzing and then monoesterifying the product provides a compound represented by the formula:

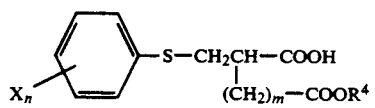
(VIII)

where $R^4$, X, m and n are as previously defined. The compound of formula (VIII) or a reactive functional derivative thereof subsequently can be reacted with an amino compound represented by the formula:

(IX)

wherein $R^1$ and $R^2$ are as previously defined, to provide a selected compound of formula (III).

The compounds of formula (IV) which have utility as starting materials in the present invention are novel compounds and can be prepared by oxidizing phenylthioalkanoic acid compounds (III).

The compounds of formula (IV) which also are alternative starting materials in the present invention are novel compounds and can be prepared by oxidizing phenylthioalkanoic acid compounds (III).

A synthesis procedure of the present invention can be conducted by dissolving a compound of formula (III) in a suitable organic solvent such as dichloromethane, then adding a molar excess (e.g., a 2.5 molar ratio) of an oxidizing agent such as m-chloroperbenzoic acid to the solution with cooling, stirring the reaction mixture for 2-3 hours with cooling or at room temperature, and working up the reaction mixture in accordance with standard methods to yield compounds of formula (I) wherein $R^3$ is a lower alkyl group. Hydrolysis of an ester product provides a compound of formula (I) in which $R^3$ is a hydrogen atom.

The compounds of formula (I) in which $R^3$ is a hydrogen atom can be converted to pharmaceutically acceptable salts using standard procedures. Present invention salts include inorganic base salts such as sodium salt or calcium salt, and organic salts which are formed with bases such as morpholine, piperidine, arginine, and the like.

Salt compounds of the present invention exhibit a similar antagonistic activity toward CCK receptors as the corresponding free carboxylic acid compounds, and thus they are useful as therapeutic agents for the prevention or treatment of irritable bowel syndrome, biliary dyskinesia and acute pancreatitis.

When the phenylsulfonylalkanoic acid compounds of formula (I) of the present invention or the pharmaceutically acceptable salts thereof are employed therapeutically, they can be administrated in various dosage forms depending upon the intended therapy. Typical dosage forms which can be used are tablets, pills, powders, granules, capsules and injectable preparations. These pharmaceutical compositions can be formulated in accordance with standard molding procedures.

The dosage of the phenylsulfonylalkanoic acid compounds of the present invention may be in the range from about 1 to 1000 mg per adult human by oral administration per day, or from about 0.1 to 100 mg per adult human by parenteral administration per day in multiple doses depending upon the type of disease, the severity of the condition to be treated, and the like.

The present invention is further illustrated in more detail by way of the following Examples and Reference Examples. The melting points of the products obtained are uncorrected.

REFERENCE EXAMPLE 1

3-(3,4-Dichlorophenylthio)-2-(2-methoxycarbonylethyl)propionic acid

A mixture of 3,4-dichlorobenzenethiol (3.00 ml), methyleneglutaronitrile (2.57 ml), ethanol (25 ml), and triton B (40% methanol solution, 10 drops) was refluxed for 4 hours. After the reaction mixture was concentrated in vacuo, the resulting residue was dissolved in chloroform, washed with water, and dried over MgSO$_4$. The solvent was evaporated at reduced pressure, and the residue was recrystallized from diethyl ether-hexane to give 6.14 g of 2-(3,4-dichlorophenylthiomethyl)glutaronitrile.

Melting point: 53°–55° C.

| Elemental Analysis (for C$_{12}$H$_{10}$Cl$_2$N$_2$S): | | | |
|---|---|---|---|
| | C % | H % | N % |
| Calcd. | 50.54 | 3.53 | 9.82 |
| Found | 50.35 | 3.39 | 9.87 |

IR (KBr): $\nu_{CN}$ 2240 cm$^{-1}$
NMR (CDCl$_3$)

δ: 1.95–2.25(2H, m), 2.45–2.75(2H, m), 2.85–2.95(1H, m), 3.10(1H, dd, J=6.6, 14.3Hz), 3.22(1H, dd, J=7.1, 14.3Hz), 7.28(1H, dd, J=1.7, 8.2Hz), 7.43(1H, d, J=8.2Hz), 7.54(1H, d, J=1.7Hz)

To a solution of 2-(3,4-dichlorophenylthiomethyl)-glutaronitrile (5.40 g) in acetic acid (36 ml) was added a concentrated hydrochloric acid (36 ml), and the mixture was refluxed for 20 hours. After the reaction mixture was concentrated in vacuo, diethyl ether was added, and the precipitates formed were filtered off. The filtrate was washed with water, and shaken with a saturated sodium bicarbonate solution. The aqueous layer was acidified with a concentrated hydrochloric acid, and extracted with diethyl ether. The organic layer was washed with water, dried over MgSO$_4$, and evaporated at reduced pressure. The residue was recrystallized from diethyl ether-hexane to give 4.44 g of 2-(3,4-dichlorophenylthiomethyl)glutaric acid.

Melting point: 112°–114° C.

| Elemental Analysis (for C$_{12}$H$_{12}$Cl$_2$O$_4$S): | | |
|---|---|---|
| | C % | H % |
| Calcd. | 44.60 | 3.74 |
| Found | 44.35 | 3.66 |

IR (KBr): $\nu_{C=O}$ 1710 cm$^{-1}$
NMR (CDCl$_3$)

δ: 1.9–2.1(2H, m), 2.25–2.5(2H, m), 2.55–2.7(1H, m), 3.01(1H, dd, J=6.0, 13.2Hz), 3.23(1H, dd, J=7.7, 13.2Hz), 7.20(1H, dd, J=2.2, 8.2Hz), 7.35(1H, d, J=8.2Hz), 7.44(1H, d, J=2.2Hz)

A mixture of 2-(3,4-dichlorophenylthiomethyl)glutaric acid (3.00 g), methanol (30 ml), and p-toluenesulfonic acid (0.09 g) was stirred at 40° C. for 2.5 hours. The reaction mixture was concentrated in vacuo, and the resulting residue was purified by flash column chromatography on silica by eluting with chloroform/ethanol (10:1) to give 2.92 g of 3-(3,4-dichlorophenylthio)-2-(2-methoxycarbonylethyl)propionic acid as an oil.

IR (neat): $\nu_{C=O}$ 1740, 1710 cm$^{-1}$
NMR (CDCl$_3$)

δ: 1.95–2.1(2H, m), 2.3–2.5(2H, m), 2.6–2.75(1H, m), 3.01(1H, dd, J=6.0, 13.2Hz), 3.23(1H, dd, J=7.7, 13.2Hz), 3.67(3H, s), 7.19(1H, dd, J=2.2, 8.2Hz), 7.36(1H, d, J=8.2Hz), 7.45(1H, d, J=2.2Hz)

REFERENCE EXAMPLE 2

The compounds in the table were prepared in a similar manner to that described in reference example 1 (all compounds were oils).

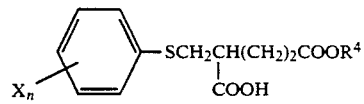

| $X_n$ | $R^4$ | IR (cm$^{-1}$) | NMR (δ, CDCl$_3$) |
|---|---|---|---|
| 3,5-dichloro | methyl | 1730, 1705 (C=O) | 1.95–2.1(2H, m), 2.3–2.5(2H, m), 2.6–2.8(1H, m), 3.04(1H, dd, J=6.0, 13.2Hz), 3.25(1H, dd, J=7.7, 13.2Hz), 3.67(3H, s), 7.1–7.25(3H, m) |
| 4-chloro | methyl | 1730, 1705 (C=O) | 1.95–2.1(2H, m), 2.3–2.5(2H, m), 2.6–2.75(1H, m), 2.99(1H, dd, J=6.0, 13.2Hz), 3.21(1H, dd, J=7.7, 13.2Hz), 3.66(3H, s), 7.2–7.35(4H, m) |
| 3-chloro | methyl | 1730, 1710 (C=O) | 1.95–2.15(2H, m), 2.3–2.5(2H, m), 2.6–2.75(1H, m), 3.02(1H, dd, J=6.0, 13.7Hz), 3.25(1H, dd, J=7.7, 13.7Hz), 3.66(3H, s), 7.15–7.3(3H, m), 7.35(1H, t, J=1.1Hz) |
| 3-bromo | methyl | 1735, 1710 (C=O) | 1.95–2.1(2H, m), 2.3–2.5 (2H m,), 2.6–2.75(1H, m), 3.02 (1H, dd, J=6.0, 13.7Hz), 3.24 (1H, dd, J=7.7, 13.7Hz), 3.67 (3H, s,) 7.16(1H, t, J=7.7Hz), 7.25–7.4(2H, m), 7.51(1H, t, J=1.7Hz) |
| 3,4-dichloro | ethyl | 1730, 1710 (C=O) | 1.24(3H, t, J=7.1Hz), 1.95–2.1 (2H, m), 2.25–2.5(2H, m), 2.6–2.75(1H, m), 3.02(1H, dd, J=6.0, 13.2Hz), 3.23(1H, dd, J=7.7, 13.2Hz), 4.12(2H, q, J=7.1Hz), 7.20(1H, dd, J=2.2, 8.2Hz), 7.36(1H, d, J=8.2Hz), 7.45(1H, d, J=2.2Hz) |

REFERENCE EXAMPLE 3

(+)-3-(3,4-Dichlorophenylthio)-2-(2-methoxycarbonylethyl)propionic acid and
(−)-3-(3,4-dichlorophenylthio)-2-(2-methoxycarbonylethyl)propionic acid A mixture of (±)-3-(3,4-dichlorophenylthio)-2-(2-methoxycarbonylethyl)propionic acid (144.1 g), quinine (161.0 g), and 2-propanol (400 ml) was heated to solution, and about 250 ml of 2-propanol was evaporated at reduced pressure. The residual solution was allowed to stand at room temperature. The precipitated crystals were collected, and further recrystallized three times from 2-propanol to give 113.0 g of the salt formed from (+)-3-(3,4-dichlorophenylthio)-2-(2-methoxycarbonylethyl)propionic acid and quinine. To this salt (0.64 g) was added a 2N hydrochloric acid (20 ml), and a separated oil was extracted with ethyl acetate. The organic layer was washed with water, dried over MgSO$_4$, and evaporated at reduced pressure to give 0.32 g of (+)-3-(3,4-dichlorophenylthio)-2-(2-methoxycarbonylethyl)propionic acid as an oil.

Specific rotation: $[\alpha]_D^{25}$ +29.4° (c=1.44, MeOH)
IR and NMR: in agreement with reference example 1.
In a further step, the above first filtrate was concentrated in vacuo and acidified with a 2N hydrochloric acid. The separated oil was extracted with ethyl acetate, washed with water, dried over MgSO$_4$, and ethyl acetate was evaporated at reduced pressure. The resulting residue (8.0 g), quinidine (7.7 g), and ethyl acetate (40 ml) was heated to solution, and about 20 ml of ethyl acetate was evaporated at reduced pressure. This residual solution was allowed to stand at room temperature. The precipitated crystals were collected, and further recrystallized from 2-propanol to give 11.7 g of the salt formed from (−)-3-(3,4-dichlorophenylthio)-2-(2-methoxycarbonylethyl)propionic acid and quinidine. To this salt (0.41 g) was added a 2N hydrochloric acid (15 ml), and a separated oil was extracted with ethyl acetate. The organic layer was washed with water, dried over MgSO$_4$, and evaporated at reduced pressure to give 0.20 g of (−)-3-(3,4-dichlorophenylthio)-2-(2-methoxycarbonylethyl)propionic acid as an oil.

Specific rotation: $[\alpha]_D^{25} -28.3°$ (c = 1.02, MeOH)

IR and NMR spectrum were in agreement with reference example 1.

REFERENCE EXAMPLE 4

3-(3,4-Dichlorophenylthio)-2-(3-methoxycarbonylpropyl)propionic acid

A mixture of 3,4-dichlorobenzenethiol (0.20 ml), di-tert-butyl 2-methyleneadipate (350 mg), ethanol (2 ml), and triton B (40% methanol solution, 2 drops) was stirred at 170° C. in a sealed tube for 17 hours. After the reaction mixture was concentrated in vacuo, the resulting residue was dissolved in chloroform, washed with a 0.5% sodium hydroxide solution, water and a saturated sodium chloride solution respectively, and dried over MgSO$_4$. The solvent was evaporated at reduced pressure, and the residue was purified by flash column chromatography on silica by eluting with diethyl ether/hexane (1:10) to give 430 mg of di-tert-butyl 2-(3,4-dichlorophenylthiomethyl)adipate as an oil.

IR (neat): $\nu_{C=O}$ 1725 cm$^{-1}$
NMR (CDCl$_3$)
δ: 1.43(9H, s), 1.47(9H, s), 1.55–1.7(4H, m), 2.15–2.25(2H, m), 2.4–2.55(1H, m), 2.94(1H, dd, J=6.0, 13.2Hz), 3.12(1H, dd, J=8.2, 13.2Hz), 7.17(1H, dd, J=2.2, 8.8Hz), 7.34(1H, d, J=8.8Hz), 7.43(1H, d, J=2.2Hz)

To a solution of di-tert-butyl 2-(3,4-dichlorophenylthiomethyl)adipate (550 mg) in benzene (7 ml) was added p-toluenesulfonic acid (40 mg), and the mixture was refluxed for 45 minutes. After the reaction mixture was cooled to room temperature, methanol (7 ml) was added, and the solution was stirred at 40° C. for 2.5 hours. The reaction mixture was concentrated in vacuo, and the resulting residue was purified by flash column chromatography on silica by eluting with chloroform/methanol (10:1) to give 340 mg of 3-(3,4-dichlorophenylthio)-2-(3-methoxycarbonylpropyl)propionic acid as an oil.

IR (neat): $\nu_{C=O}$ 1735, 1705 cm$^{-1}$
NMR (CDCl$_3$)
δ: 1.6–1.85(4H, m), 2.33(2H, t, J=6.6Hz), 2.55–2.7(1H, m), 3.00(1H, dd, J=6.0, 13.2Hz), 3.21(1H, dd, J=7.7, 13.2Hz), 3.67(3H, s), 7.19(1H, dd, J=2.2, 8.2Hz), 7.35(1H, d, J=8.2Hz), 7.44(1H, d, J=2.2Hz)

REFERENCE EXAMPLE 5

3-(3,4-Dichlorophenylthio)-2-methoxycarbonylmethylpropionic acid

A mixture of 3,4-dichlorobenzenethiol (1.15 ml), sodium 3-methoxycarbonyl-2-methylenepropionate (1.50 g), methanol (40 ml), and triton B (40% methanol solution, 5 drops) was refluxed for 20 hours. The reaction mixture was concentrated in vacuo. To the resulting residue was added a diluted hydrochloric acid, and a separated oil was extracted with diethyl ether. The organic layer was washed with water, dried over MgSO$_4$, and evaporated at reduced pressure. The residue was purified by flash column chromatography on silica by eluting with chloroform/ethanol (10:1) to give 2.34 g of 3-(3,4-dichlorophenylthio)-2-methoxycarbonylmethylpropionic acid as an oil.

IR (neat): $\nu_{C=O}$ 1740, 1710 cm$^{-1}$
NMR (CDCl$_3$)
δ: 2.65–2.9(2H, m), 3.0–3.2(2H, m), 3.3–3.45(1H, m), 3.69(3H, s), 7.20(1H, dd, J=2.2, 8.2Hz), 7.36(1H, d, J=8.2Hz), 7.46(1H, d, J=2.2Hz)

REFERENCE EXAMPLE 6

Methyl 5-(3,4-dichlorophenylthio)-4-(N,N-dipentylcarbamoyl)pentanoate

To a solution of 3-(3,4-dichlorophenylthio)-2-(2methoxycarbonylethyl)propionic acid (2.90 g) in dry benzene (50 ml) was added thionyl chloride (1.0 ml), and the reaction mixture was refluxed for 2 hours. This solution was concentrated in vacuo. The residue was dissolved in dry dichloromethane (30 ml) and added dropwise into a solution of dipentylamine (1.8 ml) and triethylamine (1.8 ml) in dry dichloromethane (50 ml) with stirring at 0° C. After stirring at room temperature for 4 hours, the reaction mixture was washed with a dilute hydrochloric acid, a saturated sodium bicarbonate solution, and water respectively, dried over MgSO$_4$, and concentrated in vacuo. The residue was purified by flash column chromatography on silica by eluting with chloroform to give 3.80 g of methyl 5-(3,4-dichlorophenylthio)-4-(N,N-dipentylcarbamoyl)pentanoate as an oil.

IR (neat): $\nu_{C=O}$ 1735, 1630 cm$^{-1}$
NMR (CDCl$_3$)
δ: 0.86(3H, t, J=7.1Hz), 0.89(3H, t, J=7.1Hz), 1.05–1 6(12H, m), 1.9–2.1(2H, m), 2.2–2.45(2H, m), 2.85–3.45(7H, m), 3.67(3H, s), 7.16(1H, dd, J=2.2, 8.2Hz), 7.34(1H, d, J=8.2Hz), 7.40(1H, d, J=2.2Hz)

REFERENCE EXAMPLE 7

The compounds in the table were prepared in a similar manner to that described in reference example 6 (all compounds were oils). The compounds with no specific rotation listed were racemates.

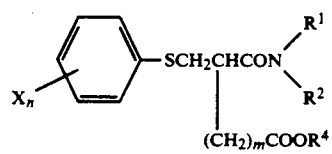

| $X_n$ | $R^1$ | $R^2$ | $R^4$ | m | Specific rotation $[\alpha]_D^{25}$ | IR (cm$^{-1}$) | NMR ($\delta$, CDCl$_3$) |
|---|---|---|---|---|---|---|---|
| 3,4-dichloro | pentyl | pentyl | methyl | 2 | +55.59° (C=1.18, MeOH) | the agreement with reference example 6 | |
| 3,4-dichloro | pentyl | pentyl | methyl | 2 | −57.64° (C=1.02, MeOH) | the agreement with reference example 6 | |
| 3,4-dichloro | 3-methoxy-propyl | pentyl | methyl | 2 | | 1730 1630 (C=O) | 0.86 and 0.89(3H, t, J=7.1Hz), 1.05-2.1(10H, m), 2.25-2.45 (2H, m), 2.85-3.5(12H, m), 3.67(3H, s), 7.16(1H, dd, J=2.2 8.8Hz), 7.34 and 7.35(1H, d, J= 8.8Hz), 7.40(1H, d, J=2.2Hz) |
| 3,4-dichloro | 3-methoxy-propyl | pentyl | methyl | 2 | +54.26° (C=1.15, MeOH) | the same as mentioned above | |
| 3,4-dichloro | 3-methoxy-propyl | pentyl | methyl | 2 | −52.23° (C=1.03, MeOH) | the same as mentioned above | |
| 3,5-dichloro | pentyl | pentyl | methyl | 2 | | 1740 1640 (C=O) | 0.86(3H, t, J=7.2Hz), 0.89(3H, t, J=6.6Hz), 1.05-1.6(12H, m), 1.9-2.1(2H, m), 2.25-2.5(2H, m), 2.9-3.45(7H, m), 3.68(3H, s, 7.1-7.2(3H, m) |
| 4-chloro | pentyl | pentyl | methyl | 2 | | 1735 1635 (C=O) | 0.86(3H, t, J=7.1Hz), 0.89(3H, t, J=7.1Hz), 1.0-1.55(12H, m), 1.95-2.45(4H, m), 2.8-3.4(7H, m), 3.66(3H, s), 7.2-7.3(4H, m) |
| 3-chloro | pentyl | pentyl | methyl | 2 | | 1735 1640 (C=O) | 0.85(3H, t, J=7.1Hz), 0.89(3H, t, J=7.1Hz), 1.05-1.6(12H, m), 1.9-2.1(2H, m), 2.25-2.5(2H, m), 2.85-3.4(7H, m), 3.67(3H, s), 7.1-7.35(4H, m) |
| 3-bromo | pentyl | pentyl | methyl | 2 | | 1735 1640 (C=O) | 0.85(3H, t, J=7.1Hz), 0.89(3H, t, J=7.1Hz), 1.05-1.6(12H, m), 1.95-2.1(2H, m), 2.2-2.5(2H, m), 2.85-3.4(7H, m), 3.67(3H, s), 7.14(1H, t, J=7.7Hz), 7.2 7.35(2H, m), 7.45(1H, t, J= 1.7Hz) |
| 3,4-dichloro | pentyl | pentyl | methyl | 3 | | 1740 1640 (C=O) | 0.87(3H, t, J=7.1Hz), 0.89(3H, t, J=7.1Hz), 1.05-1.75(16H, m), 2.2-2.4(2H, m), 2.75-2.9 (1H, m), 2.95-3.4(6H, m), 3.67 (3H, s), 7.14(1H, dd, J=2.2, 8.2Hz), 7.34(1H, d, J=8.2Hz), 7.38(1H, d, J=2.2Hz) |
| 3,4-dichloro | pentyl | pentyl | methyl | 1 | | 1735 1640 (C=O) | 0.86(3H, t, J=7.1Hz), 0.88(3H, t, J=7.1Hz), 1.05-1.6(12H, m), 2.69(1H, dd, J=5.5, 16.5Hz), 2.78(1H, dd, J=6.6, 16.5Hz), 3.0-3.3(7H, m), 3.69(3H, s), 7.20 (1H, dd, J=2.2, 8.2Hz), 7.36(1H, d, J=8.2Hz), 7.46(1H, d, J= 2.2Hz) |
| 3,4-dichloro | methyl | butyl | methyl | 2 | | 1740 1635 (C=O) | 0.85 and 0.93(3H, t, J=7.1Hz), 1.1-1.6(4H, m), 1.8-2.1(2H, m), 2.2-2.45(2H, m), 2.85-3.4(8H, m), 3.66(3H, s), 7.15 and 7.16(1H, dd, J=2.8, 8.2Hz), 7.34(1H, d, J=8.2Hz), 7.39 and 7.40(1H, d, J=2.8Hz) |
| 3,4-dichloro | butyl | butyl | methyl | 2 | | 1735 1635 (C=O) | 0.84(3H, t, J=7.1Hz), 0.92(3H, t, J=7.1Hz), 1.1-1.55(8H, m), 1.9-2.1(2H, m), 2,2-2.5(2H, m), 2.85-3.45(7H, m), 3.67(3H, s), 7.16(1H, dd, J=2.2, 8.2Hz), 7.34(1H, d, J=8.2Hz), 7.40(1H, d, J=2.2Hz) |
| 3,4-dichloro | hexyl | hexyl | methyl | 2 | | 1735 1635 (C=O) | 0.87(6H, t, J=7.1Hz), 1.0-1.55 (16H, m), 1.9-2.1(2H, m), 2.2-2.5(2H, m), 2.85-3.45(7H, m), 3.67(3H, s), 7.15(1H, dd, J=2.2, 8.8Hz), 7.34(1H, d, J=8.8Hz), 7.39(1H, d, J=2.2Hz) |
| 3,4-dichloro | heptyl | heptyl | methyl | 2 | | 1730 1630 (C=O) | 0.8-0.95(6H, m), 1.0-1.55 (20H, m), 1.9-2.1(2H, m), 2.2-2.5(2H, m), 2.85-3.45(7H, m), 3.67(3H, s), 7.15(1H, dd, J=2.2, 8.8Hz), 7.34(1H, d, J=8.8Hz), |

-continued

| $X_n$ | $R^1$ | $R^2$ | $R^4$ | m | Specific rotation $[\alpha]_D^{25}$ | IR (cm$^{-1}$) | NMR ($\delta$, CDCl$_3$) |
|---|---|---|---|---|---|---|---|
| 3,4-dichloro | iso-pentyl | iso-pentyl | methyl | 2 | | 1740 1640 (C=O) | 7.39(1H, d, J=2.2Hz) 0.79(3H, d, J=6.6Hz), 0.80(3H, d, J=6.6Hz), 0.92(6H, d, J=6.6Hz), 1.2-1.65(6H, m), 1.9-2.1(2H, m), 2.2-2.5(2H, m), 2.85-3.45(7H, m), 3.67(3H, s), 7.15(1H, dd, J=2.2, 8.2Hz), 7.34 (1H, d, J=8.2Hz), 7.39(1H, d, J=2.2Hz) |
| 3,4-dichloro | pentyl | pentyl | ethyl | 2 | | 1730 1635 (C=O) | 0.86(3H, t, J=7.2Hz), 0.89(3H, t, J=6.6Hz), 1.05-1.6(15H, m), 1.9-2.1(2H, m), 2.2-2.45(2H, m), 2.85-3.45(7H, m), 4.13(2H, q, J=7.1Hz), 7.16(1H, dd, J=2.2, 8.2Hz), 7.34(1H, d, J=8.2Hz), 7.40(1H, d, J=2.2Hz) |

REFERENCE EXAMPLE 8

Methyl 5-(3,4-dichlorophenylsulfinyl)-4-(N,N-dipentylcarbamoyl)pentanoate

Into a solution of methyl 5-(3,4-dichlorophenylthio)-4-(N,N-dipentylcarbamoyl)pentanoate (5.12 g) in dry dichloromethane (100 ml) were added portions of m-chloroperbenzoic acid (70%, 2.65 g) with stirring at −78° C. After stirring at −78° C. for 2 hours, sodium sulfite was added. The reaction mixture was washed with a saturated sodium bicarbonate solution and water, dried over MgSO$_4$, and concentrated in vacuo. The residue was purified by flash column chromatography on silica by eluting with dichloromethane/diethyl ether/hexane (1:1:2) to give 2.39 g of methyl 5-(3,4-dichlorophenylsulfinyl)-4-(N,N-dipentylcarbamoyl)-pentanoate (diastereomer A) in a early fraction and 2.47 g of diastereomer B in a later fraction.

Diastereomer A
Melting point: 64°-65° C.

| Elemental Analysis (for C$_{23}$H$_{35}$Cl$_2$NO$_4$S): | | | |
|---|---|---|---|
| | C % | H % | N % |
| Calcd. | 56.09 | 7.16 | 2.84 |
| Found | 56.07 | 7.36 | 2.84 |

IR (KBr): $\nu_{C=O}$ 1730, 1630 cm$^{-1}$ $\nu_{SO}$ 1040 cm$^{-1}$
NMR (CDCl$_3$)
$\delta$: 0.90(3H, t, J=7.1Hz), 0.94(3H, t, J=7.1Hz), 1.2-2.1(14H, m), 2.33(2H, t, J=7.1Hz), 2.74(1H, dd, J=2.8, 12.1Hz), 3.2-3.6(6H, m), 3.66(3H, s), 7.47(1H, dd, J=2.2, 8.2Hz), 7.60(1H, d, J=8.2Hz), 7.78(1H, d, J=2.2Hz)

Diastereomer B
Property: oil
IR (neat): $\nu_{C=O}$ 1735, 1635 cm$^{-1}$ $\nu_{SO}$ 1050 cm$^{-1}$
NMR (CDCl$_3$)
$\delta$: 0.87(3H, t, J=7.1Hz), 0.94(3H, t, J=7.1Hz), 1.15-1.65(12H, m), 2.05-2.6(4H, m), 2.85-3.4(7H, m), 3.69(3H, s), 7.39(1H, dd, J=2.2, 8.2Hz), 7.58(1H, d, J=8.2Hz), 7.74(H, d, J=2.2Hz)

REFERENCE EXAMPLE 9

The compounds in the table were prepared in a similar manner to that described in reference example 8.

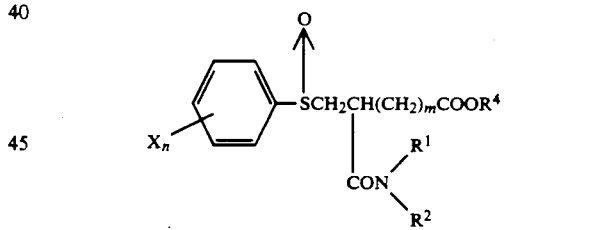

| $X_n$ | $R^1$ | $R^2$ | $R^4$ | m | diastereomer (note) | mp (°C.) (recryst. solvent) | IR (cm$^{-1}$) | NMR ($\delta$, CDCl$_3$) |
|---|---|---|---|---|---|---|---|---|
| 3,5-dichloro | pentyl | pentyl | methyl | 2 | A | oil | 1740 1635 (C=O) 1055 (S—O) | 0.85-1.0(6H, m), 1.2-2.1 (14H, m), 2.33(2H, t, J=7.2Hz), 2.75(1H, dd, J=2.7, 12.1Hz), 3.2-3.6(6H, m), 3.67 (3H, s), 7.46(1H, t, J=2.2Hz), 7.53(2H, d, J=2.2Hz) |
| 3,5-dichloro | pentyl | pentyl | methyl | 2 | B | oil | 1735 1630 (C=O) 1050 (S—O) | 0.88(3H, t, J=7.1Hz), 0.94(3H, t, J=7.1Hz), 1.15-1.7(12H, m), 2.1-2.5(4H, m), 2.92(1H, dd, J=8.2, 13.7Hz), 3.05-3.4 (6H, m), 3.69(3H, s), 7.44(1H, t, J=1.7Hz), 7.48(2H, d, J=1.7Hz) |
| 4-chloro | pentyl | pentyl | methyl | 2 | A | oil | 1740 1635 (C=O) 1045 (S—O) | 0.90(3H, t, J=7.1Hz), 0.93(3H, t, J=7.1Hz), 1.2-2.1(14H, m), 2.32(2H, t, J=7.1Hz), 2.74(1H, dd, J=3.3, 12.1Hz), 3.15-3.55 (6H, m), 3.66(3H, s), 7.45- |

-continued

| $X_n$ | $R^1$ | $R^2$ | $R^4$ | m | diastereomer (note) | mp (°C.) (recryst. solvent) | IR (cm$^{-1}$) | NMR (δ, CDCl$_3$) |
|---|---|---|---|---|---|---|---|---|
| 4-chloro | pentyl | pentyl | methyl | 2 | B | oil | 1735, 1635 (C=O), 1040 (S—O) | 7.65(4H, m) 0.87(3H, t, J=7.1Hz), 0.93(3H, t, J=7.1Hz), 1.1-1.65(12H, m), 2.1-2.5(4H, m), 2.87(1H, dd, J=8.8, 13.7Hz), 3.02(1H, dd, J=4.4, 13.7Hz), 3.1-3.4 (5H, m), 3.69(3H, s), 7.45-7.6(4H, m) |
| 3-chloro | pentyl | pentyl | methyl | 2 | A | oil | 1735, 1640 (C=O), 1045 (S—O) | 0.90(3H, t, J=7.1Hz), 0.94(3H, t, J=6.6Hz), 1.2-2.1(14H, m), 2.32(2H, t, J=7.1Hz), 2.75(1H, dd, J=2.8, 12.1Hz), 3.2-3.55 (6H, m), 3.66(3H, s), 7.4-7.55(3H, m), 7.68(1H, s) |
| 3-chloro | pentyl | pentyl | methyl | 2 | B | oil | 1735, 1630 (C=O), 1045 (S—O) | 0.87(3H, t, J=7.1Hz), 0.94(3H, t, J=7.1Hz), 1.15-1.65(12H, m), 2.15 and 2.17(2H, t, J=7.1Hz), 2.25-2.5(2H, m), 2.89 (1H, dd, J=8.8, 13.7Hz), 3.05 (1H, dd, J=4.4, 13.7Hz), 3.1-3.4(5H, m), 3.69(3H, s), 7.4-7.55(3H, m), 7.65(1H, s) |
| 3-bromo | pentyl | pentyl | methyl | 2 | A | oil | 1730, 1630 (C=O), 1040 (S—O) | 0.90(3H, t, J=7.1Hz), 0.94(3H, t, J=7.1Hz), 1.2-2.1(14H, m), 2.33(2H, t, J=7.1Hz), 2.75(1H, dd, J=2.8, 12.1Hz), 3.2-3.55 (6H, m), 3.66(3H, s), 7 38(1H, t, J=7.7Hz), 7.5-7.65(2H, m), 7.82(1H, t, J=1.7Hz) |
| 3-bromo | pentyl | pentyl | methyl | 2 | B | oil | 1735, 1635 (C=O), 1045 (S—O) | 0.87(3H, t, J=7.1Hz), 0.94(3H, t, J=7.1Hz), 1.15-1.7(12H, m), 2.15 and 2.17(2H, t, J=7.1Hz), 2.25-2.5(2H, m), 2.89 (1H, dd, J=8.8, 13.7Hz), 3.05 (1H, dd, J=4.4, 13.7Hz), 3.1-3.4(5H, m), 3.69(3H, s), 7.37 (1H, t, J=7.7Hz), 7.45-7.65 (2H, m), 7.79(1H, t, J=1.7Hz) |
| 3,4-dichloro | pentyl | pentyl | methyl | 1 | A | oil | 1735, 1640 (C=O), 1050 (S—O) | 0.8-1.0(6H, m), 1.05-1.8 (12H, m), 2.49(1H, dd, J=7.1, 15.9Hz), 2.74(1H, dd, J=6.6, 15.9Hz), 2.88(1H, dd, J=4.4, 12.6Hz), 3.1-3.45(5H, m), 3.6-3.75(4H, m), 7.44(1H, dd, J=2.2, 8.2Hz), 7.60(1H, d, J=8.2Hz), 7.76(1H, d, J=2.2Hz) |
| 3,4-dichloro | pentyl | pentyl | methyl | 1 | B | 65-68 (hexane) | 1730, 1635 (C=O), 1050 (S—O) | 0.86(3H, t, J=7.1Hz), 0.94(3H, t, J=7.1Hz), 1.1-1.75(12H, m), 2.8-3.05(4H, m), 3.1-3.35(4H, m), 3.6-3.8(4H, m), 7.40(1H, dd, J=2.2, 8.2Hz), 7.60(1H, d, J=8.2Hz), 7.74 (1H, d, J=2.2Hz) |
| 3,4-dichloro | pentyl | pentyl | methyl | 3 | A | oil | 1740, 1630 (C=O), 1050 (S—O) | 0.90(3H, t, J=7.1Hz), 0.94(3H, t, J=7.1Hz), 1.2-1.8(16H, m), 2.2-2.35(2H, m), 2.65-2.8 (1H, m), 3.2-3.55(6H, m), 3.65(3H, s), 7.45(1H, dd, J=2.2, 8.2Hz), 7.60(1H, d, J=8.2Hz), 7.76(1H, d, J=2.2Hz) |
| 3,4-dichloro | pentyl | pentyl | methyl | 3 | B | oil | 1740, 1635 (C=O), 1045 (S—O) | 0.87(3H, t, J=7.1Hz), 0.94(3H, t, J=7.1Hz), 1.15-1.90(16H, m), 2.35(2H, t, J=7.1Hz), 2.93 (1H, dd, J=8.2, 13.7Hz), 3.05-3.35(6H, m), 3.68(3H, s), 7.37(1H, dd, J=2.2, 8.2Hz), 7.57(1H, d, J=8.2Hz), 7.73(1H, d, J=2.2Hz) |
| 3,4-dichloro | butyl | butyl | methyl | 2 | A | oil | 1740, 1640 (C=O), 1050 (S—O) | 0.85-1.05 (6H, m), 1.2-2.15 (10H, m), 2.33(2H, t, J=7.1Hz), 2.74(1H, dd, J=2.7, 12.1Hz), 3.2-3.6(6H, m), 3.67 (3H, s), 7.46(1H, dd, J=2.2, 8.2Hz), 7.60(1H, d, J=8.2Hz), 7.77(1H, d, J=2.2Hz) |
| 3,4-dichloro | butyl | butyl | methyl | 2 | B | oil | 1735, 1630 (C=O), 1050 | 0.90(3H, t, J=7.1Hz), 0.97(3H, t, J=7.1Hz), 1.15-1.7(8H, m), 2.05-2.5(4H, m), 2.91(1H, dd, J=7.7, 13.7Hz), 3.0-3.4 |

-continued

| $X_n$ | $R^1$ | $R^2$ | $R^4$ | m | diastereomer (note) | mp (°C.) (recryst. solvent) | IR $(cm^{-1})$ | NMR ($\delta$, $CDCl_3$) |
|---|---|---|---|---|---|---|---|---|
| | | | | | | | (S—O) | (6H, m), 3.69(3H, s), 7.38(1H, dd, J=2.2, 8.2Hz), 7.58(1H, d. J=8.2Hz), 7.74(1H, d, J=2.2Hz) |
| 3,4-dichloro | hexyl | hexyl | methyl | 2 | A | oil | 1740 1640 (C=O) 1050 (S—O) | 0.8-1.0(6H, m), 1.2-2.1 (18H, m), 2.32(2H, t, J= 7.1Hz), 2.74(1H, dd, J=2.8, 12.1Hz), 3.2-3.6(6H, m), 3.66 (3H, s), 7.46(1H, dd, J=2.2, 8.2Hz), 7.60(1H, d, J=8.2Hz), 7.77(1H, d, J=2.2Hz) |
| 3,4-dichloro | hexyl | hexyl | methyl | 2 | B | 77-78 (diethyl ether-hexane) | 1725 1625 (C=O) 1060 (S—O) | 0.8-1.0(6H, m), 1.15-1.7 (16H, m), 2.05-2.5(4H, m), 2.91(1H, dd, J=8.2, 13.7Hz), 3.0-3.4(6H, m), 3.69(3H, s), 7.38(1H, dd, J=2.2, 8.2Hz), 7.57(1H, d, J=8.2Hz), 7.73(1H, d, J=2.2Hz) |
| 3,4-dichloro | pentyl | pentyl | ethyl | 2 | A | oil | 1730 1630 (C=O) 1050 (S—O) | 0.90(3H, t, J=7.1Hz), 0.94(3H, t, J=6.6Hz), 1.15-2.1(17H, m), 2.31(2H, t, J=7.1Hz), 2.75 (1H, dd, J=3.3, 12.1Hz)), 3.15-3.6(6H, m), 4.12(2H, q, J= 7.1Hz), 7.47(1H, dd, J=2.2, 8.2 Hz), 7.60(1H, d, J=8.2Hz), 7.78(1H, d, J=2.2Hz) |

(note)
Diastereomer A is a product isolated by flash column chromatography on silica in a early fraction and diastereomer B is a product in a later fraction.

REFERENCE EXAMPLE 10

Methyl 5-(3,4-dichlorophenylthio)-4-(N-pentyl-N-phenethyl-carbamoyl)pentanoate

To a solution of 3-(3,4-dichlorophenylthio)-2-(2-methoxycarbonylethyl)propionic acid (190 mg) in dry benzene (3 ml) was added thionyl chloride (0.1 ml), and the mixture was refluxed for 2 hours. The reaction mixture was concentrated in vacuo, and the residue which was dissolved in dry dichloromethane (3 ml) was added dropwise into a solution of N-pentylphenethylamine (110 mg) and triethylamine (0.1 ml) in dry dichloromethane (3 ml) with stirring at 0° C. After stirring at room temperature for 4 hours, the reaction mixture was washed with a dilute hydrochloric acid, water, a saturated sodium bicarbonate solution, and water respectively, dried over $MgSO_4$, and concentrated in vacuo. The residue was purified by flash column chromatography on silica by eluting with dichloromethane/diethyl ether/hexane (1:1:4) to give 280 mg of methyl 5-(3,4-dichlorophenylthio)-4-(N-pentyl-N-phenethylcarbamoyl)pentanoate as an oil.

IR (neat): $\nu_{C=O}$ 1730, 1635 $cm^{-1}$

NMR ($CDCl_3$) $\delta$: 0.84 and 0.89 (3H, t, J=6,6Hz), 1.0-1.6(6H, m), 1.85-2.1(2H, m), 2.2-2.45(2H, m), 2.65-3.7(12H, m), 6.97(1H, d, J=6.6Hz), 7.1-7.4(7H, m)

REFERENCE EXAMPLE 11

The compounds in the table were prepared in a similar manner to that described in reference example 10 (all compounds were oils)

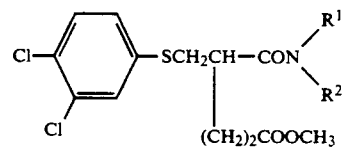

| $R^1$ | $R^2$ | IR $(cm^{-1})$ | NMR ($\delta$, $CDCl_3$) |
|---|---|---|---|
| pentyl | 3-phenyl-propyl | 1730, 1630 (C=O) | 0.85 and 0.87(3H, t, J=6.6 Hz), 1.0-1.55(6H, m), 1.7-2.1(4H, m), 2.2-2.65 (4H, m), 2.8-3.45(7H, m), 3.63 and 3.66(3H, s), 7.05-7.4(8H, m) |
| phenethyl | phenethyl | 1730, 1635 (C=O) | 1.85-2.05(2H, m), 2.15-2.4(2H, m), 2.55-3.7(14H, m), 6.93(2H, d, J=6.6Hz), 7.12(1H, dd, J=2.2, 8.8 Hz), 7.15-7.35(9H, m), 7.38 (1H, d, J=2.2Hz) |
| 3-phenyl-propyl | 3-phenyl-propyl | 1735, 1635 (C=O) | 1.7-2.05(6H, m), 2.15-2.4 (2H, m), 2.46(2H, t, J=7.7 Hz), 2.59(2H, t, J=7.7Hz), 2.8-3.45(7H, m), 3.62(3H, s), 7.0-7.4(13H, m) |
| hexyl | 4-phenyl-butyl | 1735, 1635 (C=O) | 0.87(3H, t, J=7.2Hz), 1.0-1.7(12H, m), 1.85-2.1 (2H, m), 2.15-2.7(4H, m), 2.85-3.45(7H, m), 3.65 and 3.66(3H, s), 7.1-7.4(8H, m) |
| methyl | benzyl | 1730, 1670, 1635 (C=O) | 1.9-2.5(4H, m), 2.8-3.35 (6H, m), 3.60 and 3.65(3H, s), 4.35-4.75(2H, m), 7.0-7.4(8H, m) |

REFERENCE EXAMPLE 12

Methyl 5-(3,4-dichlorophenylsulfinyl)-4-(N-pentyl-N-phenethylcarbamoyl)pentanoate

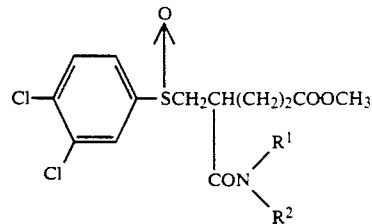

Into a solution of methyl 5-(3,4-dichlorophenylthio)-4-(N-pentyl-N-phenethylcarbamoyl)pentanoate (280 mg) in dry chloroform (10 ml) were added portions of m-chloroperbenzoic acid (70%, 140 mg) with stirring at −78° C. After stirring at −78° C. for 2 hours, sodium sulfite was added. The reaction mixture was washed with a saturated sodium bicarbonate solution and water, dried over MgSO$_4$, and concentrated in vacuo. The residue was purified by flash column chromatography on silica by eluting with dichloromethane/diethyl ether/hexane (1:1:2) to give 100 mg of methyl 5-(3,4-dichlorophenylsulfinyl)-4-(N-pentyl-N-phenethylcarbamoyl)pentanoate (diastereomer A) in a early fraction and 110 mg of diastereomer B in a later fraction.

Diastereomer A
Property: oil
IR(neat) $\nu_{C=O}$ 1735, 1630 cm$^{-1}$ $\nu_{SO}$ 1050 cm$^{-1}$
NMR (CDCl$_3$) δ: 0.90 and 0.92(3H, t, J=7.1Hz), 1.2-2.05(8H, m), 2.28(2H, t, J=7.1Hz), 2.7-3.05(3H, m), 3.15-3.85(9H, m), 7.15-7.4(5H, m), 7.46(1H, dd, J=1.7, 8.2Hz), 7.60(1H, d, J=8.2Hz), 7.77(1H, d, J=1.7Hz)

Diastereomer B
Property: oil
IR (neat): $\nu_{C=O}$ 1740, 1630 cm$^{-1}$ $\nu_{SO}$ 1045 cm$^{-1}$
NMR (CDCl$_3$)
δ: 0.87 and 0.92(3H, t, J=7.1Hz), 1.15-1.65(8H, m), 2.05-2.45(4H, m), 2.7-3.0(3H, m), 3.1-3.6(4H, m), 3.66 and 3.69(3H, s), 7.1-7.45(6H, m), 7.57 and 7.59(1H, d, J=8.2Hz), 7.73(1H, d, J=1.6Hz)

REFERENCE EXAMPLE 13

The compounds in the table were prepared in a similar manner to that described in reference example 12 (all compounds were oils).

| R$^1$ | R$^2$ | diastereomer (note) | IR (cm$^{-1}$) | NMR (δ, CDCl$_3$) |
|---|---|---|---|---|
| pentyl | 3-phenylpropyl | A | 1735, 1630 (C=O) 1045 (S—O) | 0.88 and 0.92(3H, t, J=6.6Hz), 1.15-2.4(12H, m), 2.55-2.8(3H, m), 3.15-3.7(9H, m), 7.15-7.4(5H, m), 7.45 and 7.46(1H, dd, J=1.7, 8.2Hz), 7.60(1H, d, J=8.2Hz), 7.76 and 7.77(1H, d, J=1.7Hz) |
| pentyl | 3-phenylpropyl | B | 1730, 1630 (C=O) 1045 (S—O) | 0.85 and 0.92(3H, t, J=7.1Hz), 1.1-2.5(12H, m), 2.56 and 2.65(2H, t, J=7.7Hz), 2.89(1H, dd, J=8.2, 13.7Hz), 3.0-3.35(6H, m), 3.66 and 3.68(3H, s), 7.1-7.4(6H, m), 7.55 ad 7.56(1H, d, J=8.2Hz), 7.73 (1H, d, J=2.2Hz) |
| phenethyl | phenethyl | A | 1730, 1635 (C=O) 1050 (S—O) | 1.7-2.0(2H, m), 2.23(2H, t, J=7.1Hz), 2.74(1H, dd, J=3.3, 12.1Hz), 2.8-3.0(4H, m), 3.15-3.9(9H, m), 7.15-7.4(10H, m), 7.46(1H, dd, J=2.2, 8.2Hz), 7.60 (1H, d, J=8.2Hz), 7.77(1H, d, J=2.2Hz) |
| phenethyl | phenethyl | B | 1735, 1635 (C=O) 1050 (S—O) | 2.0-2.35(4H, m), 2.65-2.85(6H, m), 3.15-3.7(8H, m), 7.1-7.75(13H, m) |
| 3-phenylpropyl | 3-phenylpropyl | A | 1740, 1640 (C=O) 1055 (S—O) | 1.7-2.35(8H, m), 2.55-2.75(5H, m), 3.2-3.6(6H, m), 3.62(3H, s), 7.15-7.35(10H, m), 7.45(1H, dd, J=2.2, 8.2Hz), 7.59(1H, d, J=8.2Hz), 7.77(1H, d, J=2.2Hz) |
| 3-phenylpropyl | 3-phenylpropyl | B | 1730, 1635 (C=O) 1045 (S—O) | 1.6-2.15(6H, m), 2.2-2.45(2H, m), 2.53(2H, t, J=7.7Hz), 2.62(2H, t, J=7.7Hz), 2.87(1H, dd, J=7.7, 13.7Hz), 3.05-3.35(6H, m), 3.65(3H, s), 7.1=7.4 (11H, m), 7.54(1H, d, J=8.2Hz), 7.72(1H, d, J=2.2Hz) |

(note)
Diastereomer A is a product isolated by flash column chromatography on silica in a early fraction and diastereomer B is a product in a later fraction.

REFERENCE EXAMPLE 14

3-(3,4-Dimethylphenylthio)-2-(2-methoxycarbonylethyl)propionic acid

A mixture of 3,4-dimethylbenzenethiol (0.59 ml), 2-methyleneglutaronitrile (0.48 ml), ethanol (10 ml), and triton B (40% ethanol solution, 5 drops) was refluxed for 5 hours. After the reaction mixture was concentrated in vacuo, the resulting residue was dissolved in chloroform, washed with water, and dried over MgSO$_4$. The solvent was evaporated at reduced pressure, and the residue was purified by flash column chromatography on silica by eluting with benzene/ethyl acetate (7:1) to give 1.18 g of 2-(3,4-dimethylphenylthiomethyl)glutaronitrile as an oil.

IR (neat): $\nu_{CN}$ 2230 cm$^{-1}$
NMR (CDCl$_3$)
δ: 1.9-2.35(8H, m), 2.45-2.7(2H, m), 2.85-2.9(1H, m), 2.98(1H, dd, J=7.7, 13.7Hz), 3.18(1H, dd, J=6.6, 13.7Hz), 7.11(1H, d, J=7.7Hz), 7.19(1H, dd, J=1.7, 7.7Hz), 7.24(1H, d, J=1.7Hz)

To a solution of 2-(3,4-dimethylphenylthiomethyl)glutaronitrile (1.16 g) in acetic acid (8 ml) was added a concentrated hydrochloric acid (8 ml), and the mixture was refluxed for 19 hours. After the reaction mixture was concentrated in vacuo, diethyl ether was added, and the precipitated solids were filtered off. The filtrate was washed with water, and shaken with a saturated sodium bicarbonate solution. The aqueous layer was acidified with a concentrated hydrochloric acid, and extracted with diethyl ether. The organic layer was washed with water, dried over MgSO₄, and evaporated at reduced pressure. The residue was recrystallized from diethyl ether-hexane to give 1.18 g of 2-(3,4-dimethylphenylthiomethyl)glutaric acid.

Melting point: 96°-98° C.

| Elemental Analysis (for C₁₄H₁₈O₄S): | | |
|---|---|---|
| | C % | H % |
| Calcd. | 59.55 | 6.43 |
| Found | 59.38 | 6.56 |

IR (KBr): $\nu_{C=O}$ 1705 cm⁻¹
NMR (DMSO-d₆)

δ: 1.65-1.95(2H, m), 2.1-2.55(9H, m), 3.04(2H, d, J=7.2Hz), 7.0-7.2(3H, m), 12.28(2H, s)

A mixture of 2-(3,4-dimethylphenylthiomethyl)glutaric acid (1.16 g), methanol (20 ml), and p-toluenesulfonic acid (0.04 g) was stirred at 40° C. for 1.5 hours. The reaction mixture was concentrated in vacuo, and the residue was purified by flash column chromatography on silica by eluting with chloroform/ethanol (10:1) to give 0.98 g of 3-(3,4-dimethylphenylthio)-2-(2-methoxycarbonylethyl)propionic acid as an oil.

IR (neat): $\nu_{C=O}$ 1735, 1705 cm⁻¹
NMR (CDCl₃)

δ: 1.9-2.5(10H, m), 2.55-2.7(1H, m), 2.94(1H, dd, J=6.6, 13.7Hz), 3.19(1H, dd, J=7.7, 13.7Hz), 3.65(3H, s), 7.06(1H, d, J=7.7Hz), 7.1-7.2(2H, m)

REFERENCE EXAMPLE 15

The compounds in the table were prepared in a similar manner to that described in reference example 14.

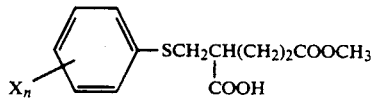

| Xₙ | mp (°C.) (recryst. solvent) | IR (cm⁻¹) | NMR (δ, CDCl₃) |
|---|---|---|---|
| 4-methyl | oil | 1735, 1710 (C=O) | 1.95-2.15(2H, m), 2.25-2.5 (5H, m), 2.55-2.7(1H, m), 2.95(1H, dd, J=6.6, 13.2 Hz), 3.19(1H, dd, J=7.7, 13.2Hz), 3.65(3H, s), 7.11(2H, d, J=7.7Hz), 7.27(2H, d, J=7.7Hz) |
| 4-nitro | oil | 1735, 1710 (C=O) 1510 (NO₂) | 2.0-2.2(2H, m), 2.35-2.55 (2H, m), 2.7-2.85(1H, m), 3.16(1H, dd, J=6.6, 13.2 Hz), 3.36(1H, dd, J=7.7, 13.2Hz), 3.68(3H, s), 7.35-7.45(2H, m), 8.1-8.2 (2H, m) |
| 4-acetyl | 59.5-61.0 (dichloromethane-hexane) | 1725, 1690 1680 (C=O) | 1.95-2.15(2H, m), 2.35-2.5 (2H, m), 2.57(3H, s), 2.7-2.85(1H, m), 3.11(1H, dd, J=6.6, 13.7Hz), 3.33(1H, dd, J=7.7, 13.7Hz), 3.67 (3H, s), 7.37(2H, d, J=8.8 Hz), 7.88(2H, d, J=8.8Hz) |

REFERENCE EXAMPLE 16

Methyl 5-(3,4-dimethylphenylthio)-4-(N,N-dipentylcarbamoyl)pentanoate

To a solution of 3-(3,4-dimethylphenylthio)-2-(2-methoxycarbonylethyl)propionic acid (0.50 g) in dry benzene (6 ml) was added thionyl chloride (0.2 ml), and the reaction mixture was refluxed for 2 hours This solution was concentrated in vacuo. The residue was dissolved in dry dichloromethane (4 ml) and added dropwise into a solution of dipentylamine (0.35 ml) and triethylamine (0.3 ml) in dry dichloromethane (2 ml) with stirring at 0° C. After stirring at room temperature for 5 hours, the reaction mixture was washed with a dilute hydrochloric acid, water, a saturated sodium bicarbonate solution, and water respectively, dried over MgSO₄, and concentrated in vacuo. The residue was purified by flash column chromatography on silica by eluting with chloroform to give 0.76 g of methyl 5-(3,4-dimethylphenylthio)-4-(N,N-dipentylcarbamoyl)pentanoate as an oil.

IR (neat): $\nu_{C=O}$ 1730, 1635 cm⁻¹
NMR (CDCl₃)

δ: 0.84(3H, t, J=6.6Hz), 0.89(3H, t, J=6.6Hz), 0.95-1.6(12H, m), 1.95-2.1(2H, m), 2.15-2.5(8H, m), 2.8-3.4(7H, m), 3.65(3H, s), 7.0-7.2(3H, m)

REFERENCE EXAMPLE 17

The compunds in the table were prepared in a similar manner to that described in reference example 16 (all compounds were oils).

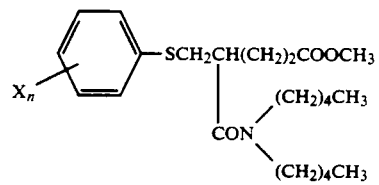

| Xₙ | IR (cm⁻¹) | NMR (δ, CDCl₃) |
|---|---|---|
| 4-methyl | 1730, 1635 (C=O) | 0.84(3H, t, J=7.1Hz), 0.89(3H, t, J=7.1 Hz), 0.95-1.6(12H, m), 1.95-2.1(2H, m), 2.15-2.45(5H, m), 2.75-3.4(7H, m), 3.65 (3H, s), 7.10(2H, d, J=8.2Hz), 7.27(2H, d, J=8.2Hz) |
| 4-nitro | 1735, 1635 (C=O) 1515 (NO₂) | 0.81(3H, t, J=6.6Hz), 0.88(3H, t, J=6.6 Hz), 1.0-1.6(12H, m), 1.9-2.15(2H, m), 2.25-2.5(2H, m), 3.0-3.45(7H, m), 3.69(3H, s), 7.35(2H, d, J=8.8Hz), 8.13(2H, d, J=8.8Hz) |
| 4-acetyl | 1735, 1685 1635 (C=O) | 0.80(3H, t, J=6.6Hz), 0.89(3H, t, J=6.6 Hz), 1.0-1.6(12H, m), 1.9-2.1(2H, m), 2.25-2.5(2H, m), 2.56(3H, s), 2.9-3.45(7H, m), 3.67(3H, s), 7.32(2H, d, J= 8.2Hz), 7.86(2H, d, J=8.2Hz) |

REFERENCE EXAMPLE 18

Methyl 5-(3,4-dimethylphenylsufinyl)-4-(N,N-dipentylcarbamoyl)pentanoate

Into a solution of methyl 5-(3,4-dimethylphenylthio)-4-(N,N-dipentylcarbamoyl)pentanoate (0.55 g) in dry dichloromethane (10 ml) were added portions of m-chloroperbenzoic acid (70%, 0.31 g) with stirring at −78° C. After stirring at −78° C. for 3 hours, sodium sulfite was added. The reaction mixture was washed with a saturated sodium bicarbonate solution and water, dried over MgSO₄, and concentrated in vacuo. The residue was purified by flash column chromatography on silica by eluting with benzene/ethyl acetate (2:1) to give 0.12 g of methyl 5-(3,4-dimethylphenylsulfinyl)-4-(N,N-dipentylcarbamoyl)pentanoate (diastereomer A) in a early fraction and 0.36 g of diastereomer B in a later fraction.

Diastereomer A
Property: oil
IR (neat): $\nu_{C=O}$ 1730, 1630 cm$^{-1}$ $\nu_{SO}$ 1045 cm$^{-1}$
NMR (CDCl₃)
δ: 0.90(3H, t, J=6.6Hz), 0.93(3H, t, J=6.6Hz), 1.1–2.45(22H, m), 2.76(1H, dd, J=3.3, 12.1Hz), 3.1–3.5(6H, m), 3.65(3H, s), 7.2–7.45(3H, m)

Diastereomer B
Property: oil
IR (neat): $\nu_{C=O}$ 1735, 1635 cm$^{-1}$ $\nu_{SO}$ 1045 cm$^{-1}$
NMR (CDCl₃)
δ: 0.87(3H, t, J=7.1Hz), 0.93(3H, t, J=7.1Hz), 1.15–1.65(12H, m), 2.1–2.5(10H, m), 2.82(1H, dd, J=9.3, 13.2Hz), 2.97(1H, dd, J=3.8, 13.2Hz), 3.1–3.45(5H, m), 3.68(3H, s), 7.2–7.45(3H, m)

REFERENCE EXAMPLE 19

The compounds in the table were prepared in a similar manner to that described in reference example 18 (all compounds were oils)

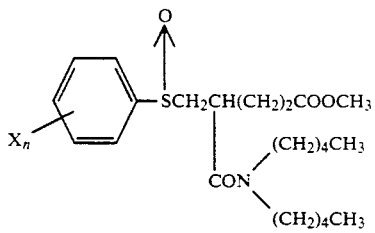

| $X_n$ | Diastereomer (note) | IR (cm$^{-1}$) | NMR (δ, CDCl₃) |
|---|---|---|---|
| 4-methyl | A | 1740, 1635 (C=O) 1045 (S—O) | 0.90(3H, t, J=7.1Hz), 0.93(3H, t, J=7.1Hz), 1.15–2.1(14H, m), 2.25–2.45(5H, m), 2.76(1H, dd, J=3.3, 12.1Hz), 3.1–3.5(6H, m), 3.65(3H, s), 7.32(2H, d, J=8.2Hz), 7.53(2H, d, J=8.2Hz) |
| 4-methyl | B | 1730, 1635 (C=O) 1040 (S—O) | 0.87(3H, t, J=7.1Hz), 0.93(3H, t, J=7.1Hz), 1.1–1.7(12H, m), 2.1–2.5(7H, m), 2.83(1H, dd, J=9.3, 13.7Hz), 2.98(1H, dd, J=3.8, 13.7Hz), 3.1–3.45(5H, m), 3.68(3H, s), 7.31(2H, d, J=8.2Hz), 7.49(2H, d, J=8.2Hz) |
| 4-nitro | A | 1735, 1635 (C=O) 1525 (NO₂) 1045 (S—O) | 0.91(3H, t, J=7.1Hz), 0.94(3H, t, J=7.1Hz), 1.2–2.1(14H, m), 2.33(2H, t, J=7.2Hz), 2.77(1H, dd, J=2.8, 12.1Hz), 3.2–3.6(6H, m), 3.66(3H, s), 7.86(2H, d, J=8.8Hz), 8.38(2H, d, J=8.8Hz) |
| 4-nitro | B | 1730, 1630 (C=O) 1525 (NO₂) 1050 (S—O) | 0.86(3H, t, J=7.1Hz), 0.94(3H, t, J=7.1Hz), 1.1–1.7(12H, m), 2.1–2.55(4H, m), 2.9–3.45(7H, m), 3.70(3H, s), 7.80(2H, d, J=8.8Hz), 8.36(2H, d, J=8.8Hz) |
| $X_n$ | Diastereomer (note) | IR (cm$^{-1}$) | NMR (δ, CDCl₃) |
| | | (S—O) | |

(note) Diastereomer A is a product isolated by flash column chromatography on silica in a early fraction and diastereomer B is a product in a later fraction.

EXAMPLE 1

Methyl 5-(3,4-dichlorophenylsulfonyl)-4-(N,N-dipentylcarbamoyl)pentanoate

Into a solution of methyl 5-(3,4-dichlorophenylthio)-4-(N,N-dipentylcarbamoyl)pentanoate (54.3 g) in dry dichloromethane (500 ml) were added portions of m-chloroperbenzoic acid (80%, 59.5 g) with stirring at 0° C. After stirring at room temperature for 4 hours, sodium sulfite was added. The reaction mixture was washed with a saturated sodium bicarbonate solution and water, dried over MgSO₄, and concentrated in vacuo. The residue was recrystallized from hexane to give 49.5 g of methyl 5-(3,4-dichlorophenylsulfonyl)-4-(N,N-dipentylcarbamoyl)pentanoate.

Melting point: 52°–54° C.

| Elemental Analysis (for C₂₃H₃₅Cl₂NO₅S): | | | |
|---|---|---|---|
| | C % | H % | N % |
| Calcd. | 54.33 | 6.94 | 2.75 |
| Found | 54.28 | 6.98 | 2.51 |

IR (KBr): $\nu_{C=O}$ 1735, 1635 cm$^{-1}$ $\nu_{SO_2}$ 1325, 1170 cm$^{-1}$
NMR (CDCl₃)
δ: 0.88(3H, t, J=7.1Hz), 0.95(3H, t, J=7.1Hz), 1.15–2.1(14H, m), 2.33(2H, t, J=7.7Hz), 3.0–3.45(6H, m), 3.68(3H, s), 3.83(1H, dd, J=8.8, 14.3Hz), 7.63(1H, d, J=8.2Hz), 7.72(1H, dd, J=1.7, 8.2Hz), 7.97(1H, d, J=1.7Hz)

EXAMPLE 2

Methyl 5-(3,4-dichlorophenylsulfonyl)-4-(N,N-dipentylcarbamoyl)pentanoate

Into a solution of methyl 5-(3,4-dichlorophenylsulfinyl)-4-(N,N-dipentylcarbamoyl)pentanoate (95 mg) in dry dichloromethane (10 ml) were added portions of m-chloroperbenzoic acid (80%, 51 mg) with stirring at 0° C. After stirring at room temperature for 2 hours, sodium sulfite was added. The reaction mixture was washed with a saturated sodium bicarbonate solution and water, dried over MgSO₄, and concentrated in vacuo. The residue was recrystallized from hexane to give 100 mg of methyl 5-(3,4-dichlorophenylsulfonyl)-4-(N,N-dipentylcarbamoyl)pentanoate. The physical properties of this compound were identical to that of the compound which was prepared in example 1.

EXAMPLE 3

The compounds in the table were prepared in a similar manner to that described in example 1 or 2. The compounds with no specific rotation listed were racemates.

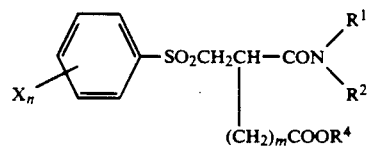

| compound No. | $X_n$ | $R^1$ | $R^2$ | $R^4$ | m | mp (°C.) (recryst. solvent) | Specific rotation $[\alpha]_D^{25}$ | IR ($cm^{-1}$) | NMR ($\delta$, $CDCl_3$) |
|---|---|---|---|---|---|---|---|---|---|
| 1 | 3,4-dichloro | pentyl | pentyl | methyl | 2 | | the reference to example 1 | | |
| 2 | 3,4-dichloro | pentyl | pentyl | methyl | 2 | oil | −1.81° (C=1.10, MeOH) | 1735 1640 (C=O) 1320 1160 ($SO_2$) | the agreement with example 1 |
| 3 | 3,4-dichloro | pentyl | pentyl | methyl | 2 | oil | +1.80° (C=1.22, MeOH) | | the agreement with the compound 2 |
| 4 | 3,4-dichloro | 3-methoxy-propyl | pentyl | methyl | 2 | oil | | 1735 1640 (C=O) 1320 1160 ($SO_2$) | 0.88 and 0.94(3H, t, J=7.1Hz), 1.15–2.1(10H, m), 2.33(2H, t, J=7.1Hz), 3.0–3.5(11H, m), 3.68(3H, s), 3.75–3.95 (1H, m), 7.63 and 7.64 (1H, d, J=8.2Hz), 7.72 and 7.73(1H, dd, J=2.2, 8.2Hz), 7.97(1H, d, J=2.2Hz) |
| 5 | 3,4-dichloro | 3-methoxy-propyl | pentyl | methyl | 2 | oil | +2.21° (C=1.63, MeOH) | | the agreement with the compound 4 |
| 6 | 3,4-dichloro | 3-methoxy-propyl | pentyl | methyl | 2 | oil | −2.13° (C=1.03, MeOH) | | the agreement with the compound 4 |
| 7 | 3,5-dichloro | pentyl | pentyl | methyl | 2 | oil | | 1735 1635 (C=O) 1320 1160 ($SO_2$) | 0.89(3H, t, J=7.1Hz), 0.95(3H, t, J=7.1Hz), 1.15–2.1(14H, m), 2.34 (2H, t, J=7.1Hz), 3.0–3.45(6H, m), 3.68(3H, s), 3.84(1H, dd, J=8.8, 14.3Hz), 7.61(1H, t, J=1.7Hz), 7.76(2H, d, J=1.7Hz) |
| 8 | 4-chloro | pentyl | pentyl | methyl | 2 | oil | | 1735 1640 (C=O) 1315 1150 ($SO_2$) | 0.89(3H, t, J=7.1Hz), 0.94(3H, t, J=7.1Hz), 1.15–2.1(14H, m), 2.33 (2H, t, J=7.2Hz), 3.05–3.45(6H, m), 3.67(3H, s), 3.78(1H, dd, J=8.3 13.7Hz), 7.52(2H, dd, J=2.2, 8.2Hz), 7.84(2H, dd, J=2.2, 8.2Hz) |
| 9 | 3-chloro | pentyl | pentyl | methyl | 2 | oil | | 1735 1635 (C=O) 1320 1150 ($SO_2$) | 0.88(3H, t, J=7.1Hz), 0.95(3H, t, J=7.1Hz), 1.15–2.1(14H, m), 2.33 (2H, t, J=7.2Hz), 3.05–3.45(6H, m), 3.68(3H, s), 3.81(1H, dd, J=8.2, 14.3Hz), 7.50(1H, t, J=7.7Hz), 7.55–7.65(1H, m), 7.75–7.85(1H, m), 7.88(1H, t, J=1.7Hz) |
| 10 | 3-bromo | pentyl | pentyl | methyl | 2 | oil | | 1740 1635 (C=O) 1320 1150 ($SO_2$) | 0.88(3H, t, J=7.1Hz), 0.95(3H, t, J=7.1Hz) 1.15–2.1(14H, m), 2.34 (2H, t, J=7.1Hz), 3.0–3.45(6H, m), 3.68(3H, s), 3.81(1H, dd, J=8.2, 13.7Hz), 7.43(1H, t, J=7.7Hz), 7.77(1H, dt, J= |

-continued

| compound No. | $X_n$ | $R^1$ | $R^2$ | $R^4$ | m | mp (°C.) (recryst. solvent) | Specific rotation $[\alpha]_D^{25}$ | IR (cm$^{-1}$) | NMR (δ, CDCl$_3$) |
|---|---|---|---|---|---|---|---|---|---|
| 11 | 3,4-dichloro | pentyl | pentyl | methyl | 1 | oil | | 1735, 1640 (C=O), 1320, 1155 (SO$_2$) | 7.7, 1.7Hz), 7.84(1H, dt, J=7.7, 1.7Hz), 8.03 (1H, t, J=1.7H) 0.88(3H, t, J=6.6Hz), 0.94(3H, t, J=6.6Hz) 1.15–1.7(12H, m), 2.74 (2H, d, J=7.2Hz), 3.1–3.35(5H, m), 3.5–3.75 (5H, m), 7.65(1H, d, J=8.2Hz), 7.73(1H, dd, J=2.2, 8.2Hz), 7.99(1H, d, J=2.2Hz) |
| 12 | 3,4-dichloro | pentyl | pentyl | methyl | 3 | oil | | 1735, 1640 (C=O), 1320, 1150 (SO$_2$) | 0.85–1.0(6H, m), 1.15–1.8(16H, m), 2.25–2.35(2H, m), 3.05–3.4 (6H, m), 3.66(3H, s), 3.85(1H, dd, J=8.8, 14.3Hz), 7.63(1H, d, J=8.2Hz), 7.72(1H, dd, J=2.2, 8.2Hz), 7.96(1H, d, J=2.2Hz) |
| 13 | 3,4-dichloro | methyl | butyl | methyl | 2 | oil | | 1735, 1640 (C=O), 1320, 1160 (SO$_2$) | 0.92 and 0.99(3H, t, J=7.1Hz), 1.2–2.1(6H, m), 2.34(2H, t, J=7.1Hz), 2.8–3.55(7H, m), 3.69(3H, s), 3.75–3.95 (1H, m), 7.6–7.75(2H, m), 7.96(1H, d, J=2.2Hz) |
| 14 | 3,4-dichloro | butyl | butyl | methyl | 2 | oil | | 1735, 1635 (C=O), 1320, 1155 (SO$_2$) | 0.91(3H, t, J=7.1Hz), 0.99(3H, t, J=7.1Hz), 1.2–2.1(10H, m), 2.34 (2H, t, J=7.1Hz), 3.0–3.45(6H, m), 3.68(3H, s), 3.84(1H, dd, J=8.8, 14.3Hz), 7.63(1H, d, J=8.2Hz), 7.73(1H, dd, J=2.2, 8.2Hz), 7.97(1H, d, J=2.2Hz) |
| 15 | 3,4-dichloro | hexyl | hexyl | methyl | 2 | oil | | 1735, 1640 (C=O), 1320, 1160 (SO$_2$) | 0.87(3H, t, J=6.6Hz), 0.92(3H, t, J=6.6Hz), 1.15–2.1(18H, m), 2.33 (2H, t, J=7.1Hz), 3.0–3.45(6H, m), 3.68(3H, s), 3.84(1H, dd, J=8.8, 14.3Hz), 7.63(1H, d, J=8.2Hz), 7.72(1H, dd, J=2.2, 8.2Hz), 7.97(1H, d, J=2.2Hz) |
| 16 | 3,4-dichloro | heptyl | heptyl | methyl | 2 | 50–52 (hexane) | | 1730, 1620 (C=O), 1310, 1145 (SO$_2$) | 0.8–1.0(6H, m), 1.15–2.1(22H, m), 2.33(2H, t, J=7.2Hz), 3.0–3.45 (6H, m), 3.68(3H, s), 3.84(1H, dd, J=8.8, 14.3Hz), 7.63(1H, d, J=8.2Hz), 7.72(1H, dd, J=2.2, 8.2Hz), 7.97(1H, d, J=2.2Hz) |
| 17 | 3,4-dichloro | iso-pentyl | iso-pentyl | methyl | 2 | oil | | 1735, 1640 (C=O), 1320, 1155 (SO$_2$) | 0.91(6H, d, J=6.6Hz), 0.98(6H, d, J=6.1Hz), 1.25–2.1(8H, m), 2.33 (2H, t, J=7.1Hz), 3.0–3.45(6H, m), 3.68(3H, s), 3.83(1H, dd, J=8.8, 14.3Hz), 7.63(1H, d, J=8.2Hz), 7.73(1H, dd, J=2.2, 8.2Hz), 7.97(1H, d, J=2.2Hz) |
| 18 | 3,4-dichloro | pentyl | pentyl | ethyl | 2 | oil | | 1730, 1640 (C=O), 1320, 1155 (SO$_2$) | 0.89(3H, t, J=6.6Hz), 0.95(3H, t, J=6.6Hz), 1.15–2.1(17H, m), 2.32 (2H, t, J=7.1Hz), 3.0–3.45(6H, m), 3.84(1H, dd, J=8.8, 14.3Hz), 4.13 (2H, q, J=7.1Hz), 7.63 (1H, d, J=8.2Hz), 7.72 (1H, dd, J=2.2, 8.2Hz), 7.97(1H, d, J=2.2Hz) |

EXAMPLE 4

5-(3,4-Dichlorophenylsulfonyl)-4-(N,N-dipentylcarbamoyl)pentanoic acid

To a solution of methyl 5-(3,4-dichlorophenylsulfonyl)-4-(N,N-dipentylcarbamoyl)pentanoate (40.3 g) in ethanol (500 ml) was added a 2N sodium hydroxide solution (40 ml). After stirring at room temperature for 16 hours, the reaction mixture was concentrated in vacuo, acidified with a dilute hydrochloric acid, and extracted with chloroform. The organic layer was washed with water, dried over MgSO$_4$, and evaporated at reduced pressure. The residue was recrystallized from diethyl ether-hexane to give 38.2 g of 5-(3,4-dichlorophenylsulfonyl)-4-(N,N-dipentylcarbamoyl)pentanoic acid.

Melting point: 76°–79° C.

| Elemental Analysis (for C$_{22}$H$_{33}$Cl$_2$NO$_5$S): | | | |
|---|---|---|---|
| | C % | H % | N % |
| Calcd. | 53.44 | 6.73 | 2.83 |
| Found | 53.17 | 6.68 | 2.76 |

IR (KBr): $\nu_{C=O}$ 1730, 1605 cm$^{-1}$ $\nu_{SO2}$ 1320, 1140 cm$^{-1}$

NMR (CDCl$_3$) δ: 0.88(3H, t, J=7.1Hz), 0.94(3H, t, J=7.1Hz), 1.15–2.1(14H, m), 2.39(2H, t, J=7.1Hz), 3.0–3.5(6H, m), 3.83(1H, dd, J=8.8, 14.3Hz), 7.63(1H, d, J=8.2Hz), 7.73(1H, dd, J=2.2, 8.2Hz), 7.97(1H, d, J=2.2Hz)

EXAMPLE 5

The compounds in the table were prepared in a similar manner to that described in example 4. The compounds with no specific rotation listed were racemates.

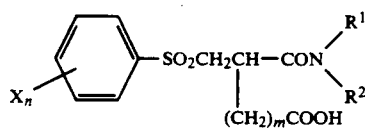

| compound No. | X$_n$ | R$^1$ | R$^2$ | m | mp (°C.) (recryst. solvent) | Specific rotation [α]$_D^{25}$ | IR (cm$^{-1}$) | NMR (δ, CDCl$_3$) |
|---|---|---|---|---|---|---|---|---|
| 19 | 3,4-dichloro | pentyl | pentyl | 2 | the reference to example 4 | | | |
| 20 | 3,4-dichloro | pentyl | pentyl | 2 | oil | −6.66° (C=1.20. MeOH) | 1725 1620 (C=O) 1320 1160 (SO$_2$) | the agreement with example 4 |
| 21 | 3,4-dichloro | pentyl | pentyl | 2 | oil | +6.60° (C=1.12, MeOH) | | the agreement with the compound 20 |
| 22 | 3,4-dichloro | 3-methoxypropyl | pentyl | 2 | 88–91 (isopropyl ether-hexane) | | 1730 1620 (C=O) 1330 1160 (SO$_2$) | 0.88 and 0.94(3H, t, J=7.1Hz), 1.15–2.1(10H, m), 2.39(2H, t, J=7.1Hz), 3.0–3.55(11H, m), 3.7–3.95(1H, m), 7.6–7.8 (2H, m), 7.97(1H, d, J=2.2Hz) |
| 23 | 3,4-dichloro | 3-methoxypropyl | pentyl | 2 | oil | −3.67° (C=1.36, MeOH) | 1730 1635 (C=O) 1330 1160 (SO$_2$) | the agreement with the compound 22 |
| 24 | 3,4-dichloro | 3-methoxypropyl | pentyl | 2 | oil | +3.23° (C=1.88, MeOH) | | the agreement with the compound 23 |
| 25 | 3,5-dichloro | pentyl | pentyl | 2 | 131–132 (diethyl ether) | | 1720 1620 (C=O) 1320 1165 (SO$_2$) | 0.89(3H, t, J=7.1Hz), 0.94(3H, t, J=7.1Hz), 1.15–2.1(14H, m), 2.40(2H, t, J=7.2Hz), 3.0–3.5(6H, m), 3.84(1H, dd, J= 8.8, 14.3Hz), 7.61(1H, t, J= 2.2Hz), 7.77(2H, d, J=2.2Hz) |
| 26 | 4-chloro | pentyl | pentyl | 2 | oil | | 1730 1635 1610 (C=O) 1315 1150 (SO$_2$) | 0.89(3H, t, J=6.6Hz), 0.93(3H, t, J=6.6Hz), 1.15–2.1(14H, m), 2.38(2H, t, J=7.1Hz), 3.05–3.5(6H, m), 3.77(1H, dd, J= 7.7, 13.7Hz), 7.52(2H, d, J= 8.8Hz), 7.84(2H, d, J=8.8Hz) |
| 27 | 3-chloro | pentyl | pentyl | 2 | 88–89.5 (diethyl ether-hexane) | | 1730 1630 (C=O) 1320 1135 (SO$_2$) | 0.88(3H, t, J=7.1Hz), 0.94(3H, t, J=7.1Hz), 1.2–2.1(14H, m), 2.39(2H, t, J=7.1Hz), 3.0–3.5(6H, m), 3.79(1H, dd, J= 8.2, 13.7Hz), 7.50(1H, t, J= 7.7Hz), 7.6–7.65(1H, m), 7.75–7.85(1H, m), 7.88(1H, t, J=1.7Hz) |
| 28 | 3-bromo | pentyl | pentyl | 2 | 93–95 | | 1725 | 0.89(3H, t, J=7.1Hz), 0.94(3H, |

| compound No. | $X_n$ | $R^1$ | $R^2$ | m | mp (°C.) (recryst. solvent) | Specific rotation $[\alpha]_D^{25}$ | IR (cm$^{-1}$) | NMR (δ, CDCl$_3$) |
|---|---|---|---|---|---|---|---|---|
| | | | | | (diethyl ether-hexane) | | 1625 (C=O) 1320 1135 (SO$_2$) | t, J=7.1Hz), 1.15-2.1(14H, m), 2.39(2H, t, J=7.1Hz), 3.0-3.5(6H, m), 3.80(1H, dd, J=8.3, 14.3Hz), 7.44(1H, t, J=7.7Hz), 7.75-7.9(2H, m), 8.03 (1H, t, J=1.7Hz) |
| 29 | 3,4-dichloro | pentyl | pentyl | 1 | 96–99 (hexane) | | 1705 1625 (C=O) 1320 1155 (SO$_2$) | 0.88(3H, t, J=7.1Hz), 0.94(3H, t, J=7.1Hz), 1.15-1.75(12H, m), 2.79(2H, d, J=5.5Hz), 3.15-3.8(7H, m), 7.66(1H, d, J=8.2Hz), 7.75(1H, d, J=8.2Hz), 8.00(1H, s) |
| 30 | 3,4-dichloro | pentyl | pentyl | 3 | 104–106 (diethyl ether-hexane) | | 1705 1635 (C=O) 1320 1150 (SO$_2$) | 0.88(3H, t, J=7.1Hz), 0.95(3H, t, J=7.1Hz), 1.2-1.8(16H, m), 2.25-2.4(2H, m), 3.05-3.35 (6H, m), 3.86(1H, dd, J=8.8, 13.7Hz), 7.63(1H, d, J=8.2Hz), 7.72(1H, dd, J=2.2, 8.2Hz), 7.96(1H, d, J=2.2Hz) |
| 31 | 3,4-dichloro | methyl | butyl | 2 | 112–113 (isopropyl ether) | | 1740 1640 1610 (C=O) 1320 1135 (SO$_2$) | 0.92 and 0.98(3H, t, J=7.1Hz), 1.2-2.1(6H, m), 2.3-2.6 (2H, m), 2.8-3.6(7H, m), 3.75-3.95(1H, m), 7.6-7.75(2H, m), 7.96(1H, d, J=2.2Hz) |
| 32 | 3,4-dichloro | butyl | butyl | 2 | oil | | 1730 1640 1610 (C=O) 1320 1160 (SO$_2$) | 0.91(3H, t, J=7.1Hz), 0.98(3H, t, J=7.1Hz), 1.2-2.1(10H, m), 2.39(2H, t, J=7.1Hz), 3.0-3.5(6H, m), 3.83(1H, dd, J=8.8, 14.3Hz), 7.63(1H, d, J=8.2Hz), 7.73(1H, dd, J=2.2, 8.2Hz), 7.97(1H, d, J=2.2Hz) |
| 33 | 3,4-dichloro | hexyl | hexyl | 2 | 67–68 (diethyl ether-hexane) | | 1720 1630 (C=O) 1325 1135 (SO$_2$) | 0.8-1.0(6H, m), 1.15-2.1 (18H, m), 2.38(2H, t, J=7.1Hz), 2.95-3.5(6H, m), 3.83 (1H, dd, J=8.2, 14.3Hz), 7.63 (1H, d, J=8.2Hz), 7.73(1H, dd, J=1.7, 8.2Hz), 7.97(1H, d, J=1.7Hz) |
| 34 | 3,4-dichloro | heptyl | heptyl | 2 | 79–81 (isopropyl ether-hexane) | | 1715 1610 (C=O) 1320 1155 (SO$_2$) | 0.8-1.0(6H, m), 1.1-2.1 (22H, m), 2.39(2H, t, J=7.1Hz), 3.0-3.5(6H, m), 3.83 (1H, dd, J=8.8, 14.3Hz), 7.63 (1H, d, J=8.2Hz), 7.72(1H, dd, J=2.2, 8.2Hz), 7.97(1H, d, J=2.2Hz) |
| 35 | 3,4-dichloro | iso-pentyl | iso-pentyl | 2 | oil | | 1720 1635 (C=O) 1320 1155 (SO$_2$) | 0.88(6H, d, J=6.6Hz), 0.94(6H, d, J=6.6Hz), 1.2-2.4(10H, m), 3.0-3.35(6H, m), 3.75-3.95 (1H, m), 7.61(1H, d, J=8.8Hz), 7.74(1H, dd, J=2.2, 8.8Hz), 7.95(1H, d, J=2.2Hz) |

EXAMPLE 6

Methyl 4-(N-benzyl--N-methylcarbamoyl)-5-(3,4-dichlorophenylsulfonyl)-pentanoate Into a solution of methyl 4-(N-benzyl-N-methylcarbamoyl)-5-(3,4-dichlorophenylthio)pentanoate (110 mg) in dry chloroform (4 ml) were added portions of m-chloroperbenzoic acid (80%, 160 mg) with stirring at 0° C. After stirring at room temperature for 4 hours, sodium sulfite was added. The reaction mixture was washed with a saturated sodium bicarbonate solution and water, dried over MgSO$_4$, and concentrated in vacuo. The residue was purified by preparative thin-layer chromatography on silica by developing with dichloromethane/diethyl ether (2:1) to give 100 mg of methyl 4-(N-benzyl-N-methylcarbamoyl)-5-(3,4-dichlorophenylsulfonyl)pentanoate as an oil.

IR (neat): $\nu_{C=O}$ 1730, 1640 cm$^{-1}$ $\nu_{SO_2}$ 1315, 1155 cm$^{-1}$

NMR (CDCl$_3$) δ: 1.75-2.4(4H, m), 2.9-3.15(4H, m), 3.45-3.7(4H, m), 3.84 and 3.94(1H, dd, J=9.3, 13.7Hz), 4.3-4.75(2H, m), 7.2-7.45(5H, m), 7.55-7.75(2H, m), 7.92 and 8.00(1H, d, J=2.2Hz)

EXAMPLE 7

Methyl 5-(3,4-dichlorophenylsulfonyl)-4-[N,N-bis(3-phenylpropyl)carbamoyl]pentanoate Into a solution of methyl 5-(3,4-dichlorophenylsulfinyl)-4-[N,N-bis(3-phenylpropyl)carbamoyl]pentanoate (220 mg) in dry dichloromethane (20 ml) were added portions of m-chloroperbenzoic acid (80%, 120 mg) with stirring at 0° C. After stirring at room temperature for 4 hours, sodium sulfite was added. The reaction mixture was washed with a saturated sodium bicarbonate solution and water, dried over MgSO$_4$, and concentrated in vacuo. The residue was purified by flash column chromatography on silica by eluting with chloroform/ethanol (50:1) to give 200 mg of methyl 5-(3,4-dichlorophenylsulfonyl)-4-[N,N-bis(3-phenylpropyl)-carbamoyl]pentanoate as an oil.

IR (neat): $\nu_{C=O}$ 1735, 1640 cm$^{-1}$ $\nu_{SO_2}$ 1320, 1160 cm$^{-1}$

NMR (CDCl$_3$) δ: 1.7-2.35(8H, m), 2.5-2.75(4H, m), 3.0-3.45(6H, m), 3.63(3H, s), 3.84(1H, dd, J=9.3, 14.3Hz), 7.05-7.35(10H, m), 7.59(1H, d, J=8.2Hz), 7.70(1H, dd, J=2.2, 8.2Hz), 7.96(1H, d, J=2.2Hz)

EXAMPLE 8

The compounds in the table were prepared in a similar manner to that described in example 6 or 7 (all compounds were oils).

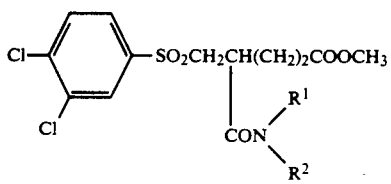

(57 mg) in ethanol (1 ml) was added a 1N sodium hydroxide solution (0.12 ml). After stirring at room temperature for 16 hours, the reaction mixture was concentrated in vacuo, acidified with a dilute hydrochloric acid, and extracted with chloroform. The organic layer was washed with water, dried over MgSO$_4$, and evaporated at reduced pressure. The residue was purified by preparative thin-layer chromatography on silica by developing with chloroform/ethanol (10:1) to give 45 mg of 5-(3,4-dichlorophenylsulfonyl)-4-(N-pentyl-N-phenethylcarbamoyl)pentanoic acid as an oil.

IR (neat): $\nu_{C=O}$ 1730, 1630, 1610 cm$^{-1}$ $\nu_{SO_2}$ 1315, 1155 cm$^{-1}$ NMR (CDCl$_3$) δ: 0.89 and 0.92(3H, t, J=7.1Hz), 1.15-2.1(8H, m), 2.31 and 2.34(2H, t, J=6.6Hz), 2.7-3.85(9H, m), 7.15-7.4(5H, m), 7.63 and 7.64(1H, d, J=8.2Hz), 7.73(1H, dd, J=2.2, 8.2Hz), 7.98 and 7.99(1H, d, J=2.2Hz)

EXAMPLE 10

The compounds in the table were prepared in a similar manner to that described in example 9.

| compound No. | R$^1$ | R$^2$ | IR (cm$^{-1}$) | NMR (δ, CDCl$_3$) |
|---|---|---|---|---|
| 36 | pentyl | phenethyl | 1730, 1635 (C=O) 1315, 1155 (SO$_2$) | 0.89 and 0.93(3H, t, J=7.1Hz), 1.2-2.1(8H, m), 2.30 (2H, t, J=7.1Hz), 2.75-3.85(12H, m), 7.15-7.4(5H, m), 7.63 and 7.64(1H, d, J=8.2Hz), 7.73(1H, dd, J=2.2, 8.2Hz), 7.98 and 7.99(1H, d, J=2.2Hz) |
| 37 | pentyl | 3-phenyl-propyl | 1730, 1635 (C=O) 1315, 1155 (SO$_2$) | 0.8-1.0(3H, m), 1.15-2.1(10H, m), 2.2-2.4(2H, m), 2.55-2.75(2H, m), 3.0-3.45(6H, m), 3.65 and 3.66(3H, s), 3.75-3.9(1H, m), 7.15-7.4(5H, m), 7.55-7.8(2H, m), 7.96(1H, d, J=2.2Hz) |
| 38 | phenethyl | phenethyl | 1725, 1635 (C=O) 1315, 1160 (SO$_2$) | 1.7-2.0(2H, m), 2.15-2.35(2H, m), 2.75-3.0(4H, m), 3.07(1H, dd, J=3.8, 13.7Hz), 3.3-3.75(9H, m), 7.15-7.4(10H, m), 7.63(1H, d, J=8.2Hz), 7.73(1H, dd, J=2.2, 8.2Hz), 7.99(1H, d, J=2.2Hz) |
| 39 | 3-phenyl-propyl | 3-phenyl-propyl | | the reference to example 7 |
| 40 | hexyl | 4-phenyl-butyl | 1735, 1640 (C=O) 1320, 1155 (SO$_2$) | 0.87 and 0.92(3H, t, J=6.6Hz), 1.2-2.1(14H, m), 2.29 and 2.33(2H, t, J=7.1Hz), 2.62 and 2.70(2H, t, J=7.1Hz), 3.0-3.45(6H, m), 3.66 and 3.67(3H, s), 3.83 (1H, dd, J=8.8, 14.3Hz), 7.1-7.35(5H, m), 7.61 and 7.62(1H, d, J=8.2Hz), 7.69 and 7.71(1H, dd, J=2.2, 8.2Hz), 7.95 and 7.97(1H, d, J=2.2Hz) |
| 41 | methyl | benzyl | | the reference to example 6 |

EXAMPLE 9

5-(3,4-Dichlorophenylsulfonyl)-4-(N-penthyl-N-phenethylcarbamoyl)pentanoic acid

To a solution of methyl 5-(3,4-dichlorophenylsulfonyl)-4-(N-pentyl-N-phenethylcarbamoyl)pentanoate

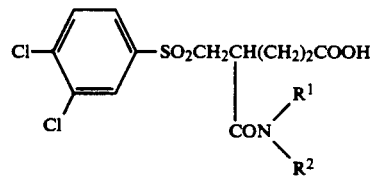

| compound No. | R$^1$ | R$^2$ | mp (°C.) (recryst. solvent) | IR (cm$^{-1}$) | NMR (δ, CDCl$_3$) |
|---|---|---|---|---|---|
| 42 | pentyl | phenethyl | | | the reference to example 9 |
| 43 | pentyl | 3-phenyl-propyl | oil | 1725, 1630 (C=O) 1315, 1155 (SO$_2$) | 0.87 and 0.91(3H, t, J=7.1Hz), 1.1-2.15 (10H, m), 2.2-2.45(2H, m), 2.5-2.75(2H, m), 2.95-3.55(6H, m), 3.65-3.9(1H, m), 7.1-7.4(5H, m), 7.55-7.75(2H, m), 7.96 (1H, d, J=1.7Hz) |
| 44 | phenethyl | phenethyl | oil | 1730, 1640 (C=O) 1320, 1160 (SO$_2$) | 1.7-2.0(2H, m), 2.1-2.4(2H, m), 2.75-3.0(4H, m), 3.06(1H, dd, J=3.8, 13.7Hz), 3.3-3.75(6H, m), 7.15-7.4(10H, m), 7.63(1H, d, J=8.2Hz), 7.73(1H, dd, J=2.2, 8.2Hz), 7.99(1H, d, J=2.2Hz) |
| 45 | 3-phenyl- | 3-phenyl- | 114-115 | 1710, 1625 | 1.65-2.4(8H, m), 2.5-2.75(4H, m), 3.03 |

| compound No. | R¹ | R² | mp (°C.) (recryst. solvent) | IR (cm⁻¹) | NMR (δ, CDCl₃) |
|---|---|---|---|---|---|
| | propyl | propyl | (diethyl ether-hexane) | (C=O) 1320, 1160 (SO₂) | (1H, dd, J=3.3, 13.7Hz), 3.1–3.4(5H, m), 3.83(1H, dd, J=8.8, 13.7Hz), 7.05–7.4(10H, m), 7.59(1H, d, J=8.2Hz), 7.69(1H, dd, J=2.2, 8.2Hz), 7.95(1H, d, J=2.2Hz) |
| 46 | hexyl | 4-phenyl-butyl | oil | 1730, 1635 (C=O) 1320, 1155 (SO₂) | 0.87 and 0.91(3H, t, J=6.6Hz), 1.15–2.1 (14H, m), 2.32 and 2.37(2H, t, J=7.1Hz), 2.55–2.75(2H, m), 3.0–3.5(6H, m), 3.7–3.9(1H, m), 7.1–7.35(5H, m), 7.61 and 7.62 (1H, d, J=8.2Hz), 7.70 and 7.71(1H, dd, J=2.2, 8.2Hz), 7.95 and 7.96(1H, d, J=2.2Hz) |
| 47 | methyl | benzyl | 110–112 (iso-propyl ether) | 1710, 1640 (C=O) 1320, 1145 (SO₂) | 1.6–2.45(4H, m), 2.9–3.2(4H, m), 3.4–4.0(2H, m), 4.3–4.75(2H, m), 7.15–7.45 (5H, m), 7.55–7.8(2H, m), 7.92 and 8.00 (1H, d, J=1.7Hz) |

EXAMPLE 11

Methyl 5-(4-acetylphenylsulfonyl)-4-(N,N-dipentylcarbamoyl)pentanoate

Into a solution of methyl 5-(4-acetylphenylthio)-4-(N,N-dipentylcarbamoyl)pentanoate (0.44 g) in dry dichloromethane (10 ml) were added portions of m-chloroperbenzoic acid (80%, 0.52 g) with stirring at 0° C. After stirring at room temperature for 2 hours, sodium sulfite was added. The reaction mixture was washed with a saturated sodium bicarbonate solution and water, dried over MgSO₄, and concentrated in vacuo. The residue was purified by flash column chromatography on silica by eluting with chloroform/ethanol (10:1) to give 0.45 g of methyl 5-(4-acetylphenylsulfonyl)-4-(N,N-dipentylcarbamoyl)pentanoate as an oil.

IR (neat): $\nu_{C=O}$ 1735, 1690, 1635 cm⁻¹ $\nu_{SO_2}$ 1320, 1150 cm⁻¹

NMR (CDCl₃) δ: 0.88(3H, t, J=7.1Hz), 0.94(3H, t, J=7.1Hz), 1.15–2.1(14H, m), 2.33(2H, t, J=7.1Hz), 2.66(3H, s), 3.0–3.5(6H, m), 3.67(3H, s), 3.82(1H, dd, J=8.2, 14.3Hz), 8.00(2H, d, J=8.2Hz), 8.10(2H, d, J=8.2Hz)

matography on silica by eluting with dichloromethane/diethyl ether (2:1) to give 0.13 g of methyl 4-(N,N-dipentylcarbamoyl)-5-(4-methylphenylsulfonyl)pentanoate as an oil.

IR (neat): $\nu_{C=O}$ 1735, 1635 cm⁻¹ $\nu_{SO_2}$ 1315, 1150 cm⁻¹

NMR (CDCl₃) δ: 0.88(3H, t, J=7.1Hz), 0.94(3H, t, J=7.1Hz), 1.15–2.1(14H, m), 2.32(2H, t, J=7.1Hz), 2.44(3H, s), 3.0–3.45(6H, m), 3.66(3H, s), 3.71(1H, dd, J=7.1, 13.7Hz), 7.34(2H, d, J=8.2Hz), 7.78(2H, d, J=8.2Hz)

EXAMPLE 13

The compounds in the table were prepared in a similar manner to that described in example 11 or 12 (all compounds were oils).

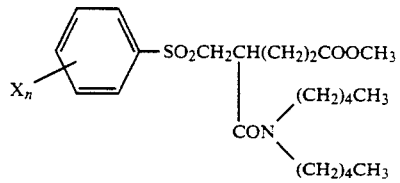

| Xn | IR (cm⁻¹) | NMR (δ, CDCl₃) |
|---|---|---|
| 3,4-dimethyl | 1730, 1635 (C=O) 1310, 1140 (SO₂) | 0.89(3H, t, J=7.1Hz), 0.94(3H, t, J=7.1Hz), 1.15–1.75(12H, m), 1.85–2.1(2H, m), 2.2–2.4(8H, m), 3.05(1H, dd, J=4.4, 13.7Hz), 3.1–3.45(5H, m), 3.6–3.75 (4H, m), 7.29(1H, d, J=8.2Hz), 7.6–7.7(2H, m) |
| 4-nitro | 1730, 1635 (C=O) 1530 (NO₂) 1310, 1155 (SO₂) | 0.88(3H, t, J=7.1Hz), 0.95(3H, t, J=7.1Hz), 1.15–2.1(14H, m), 2.34(2H, t, J=7.1Hz), 3.0–3.5(6H, m), 3.68(3H, s), 3.90(1H, dd, J=8.8, 13.7Hz), 8.10(2H, d, J=8.8Hz), 8.39(2H, d, J=8.8Hz) |

EXAMPLE 12

Methyl 4-(N,N-dipentylcarbamoyl)-5-(4-methylphenylsulfonyl)pentanoate

Into a solution of methyl 4-(N,N-dipentylcarbamoyl)-5-(4-methylphenylsulfinyl)pentanoate (0.15 g) in dry dichloromethane (5 ml) were added portions of m-chloroperbenzoic acid (80%, 0.09 g) with stirring at 0° C. After stirring at room temperature for 4 hours, sodium sulfite was added. The reaction mixture was washed with a saturated sodium bicarbonate solution and water, dried over MgSO₄, and concentrated in vacuo. The residue was purified by flash column chro-

EXAMPLE 14

5-(4-Acetylphenylsulfonyl)-4-(N,N-dipentylcarbamoyl)pentanoic acid

To a solution of methyl 5-(4-acetylphenylsulfonyl)-4-(N,N-dipentylcarbamoyl)pentanoate (0.35 g) in methanol (15 ml) was added a 1N sodium hydroxide solution (1 ml). After stirring at room temperature for hours, the reaction mixture was concentrated in vacuo, acidified with a dilute hydrochloric acid, and extracted with chloroform. The organic layer was washed with water, dried over MgSO₄, and evaporated at reduced pressure.

The residue was recrystallized from dichloromethane-hexane to give 0.27 g of 5-(4-acetylphenylsulfonyl)-4-(N,N-dipentylcarbamoyl)pentanoic acid.

Melting point: 69°-71° C.

| Elemental Analysis (for $C_{24}H_{37}NO_6S$): | | | |
|---|---|---|---|
| | C % | H % | N % |
| Calcd. | 61.64 | 7.98 | 3.00 |
| Found | 61.37 | 7.76 | 2.92 |

IR (KBr) $\nu_{C=O}$ 1720, 1680, 1610 cm$^{-1}$ $\nu_{SO2}$ 1310, 1140 cm$^{-1}$

NMR(CDCl$_3$) δ: 0.88(3H, t, J=7.1Hz), 0.94(3H, t, J=7.1Hz), 1.15-2.1(14H, m), 2.39(2H, t, J=7.1Hz), 2.66(3H, s), 3.05-3.5(6H, m), 3.81(1H, dd, J=8.2, 14.3Hz), 8.00(2H, d, J=8.2Hz), 8.10(2H, d, J=8.2Hz)

EXAMPLE 15

The compounds in the table were prepared in a similar manner to that described in example 14.

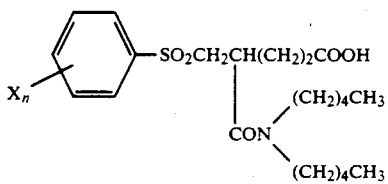

| compound No. | $X_n$ | mp (°C.) (recryst. solvent) | IR (cm$^{-1}$) | NMR (δ, CDCl$_3$) |
|---|---|---|---|---|
| 48 | 3,4-dimethyl | 77-79 (chloroform-hexane) | 1710, 1600 (C=O) 1305, 1150 (SO$_2$) | 0.89(3H, t, J=7.1Hz), 0.93(3H, t, J=7.1Hz), 1.1-2.4(22H, m), 3.06(1H, dd, J=4.4, 13.7Hz), 3.1-3.5 (5H, m), 3.67(1H, dd, J=7.7, 13.7Hz), 7.29(1H, d, J= 8.2Hz), 7.55-7.7(2H, m) |
| 49 | 4-methyl | 125-127 (dichloromethane-hexane) | 1735, 1640 (C=O) 1320, 1155 (SO$_2$) | 0.88(3H, t, J=7.1Hz), 0.93(3H, t, J=7.1Hz), 1.2-2.1(14H, m), 2.38(2H, t, J=7.2Hz), 2.44(3H, s), 3.0-3.5(6H, m), 3.69(1H, dd, J=7.1, 13.7Hz), 7.34(2H, d, J=8.2Hz), 7.78(2H, d, J=8.2Hz) |
| 50 | 4-nitro | 88-90 (diethylether-hexane) | 1710, 1605 (C=O) 1535 (NO$_2$) 1305, 1150 (SO$_2$) | 0.88(3H, t, J=6.6Hz), 0.94(3H, t, J=6.6Hz), 1.1-2.1(14H, m), 2.40(2H, t, J=7.1Hz), 3.0-3.55(6H, m), 3.89(1H, dd, J=8.8, 14.3Hz), 8.10(2H, d, J=8.8Hz), 8.39(2H, d, J=8.8Hz) |
| 51 | 4-acetyl | | | the reference to example 14 |

TEST EXAMPLE 1

CCK-Receptor Binding Assay in Pancreas

Pancreatic plasma membranes were prepared by the method of Chang et al. (Molecular Pharmacology, Vol. 30, p. 212-, 1986). Male Wistar rats were sacrificed by decapitation and the pancreas was removed. The pancreas was dissected free from adipose tissue and minced in 50 volumes ice-cold Tris-HCl buffer (50 mM, pH 7.4 at 37° C.). Homogenization was performed using ultra disperser and the homogenate was centrifuged at 50,000×g for 10 minutes. The pellet was washed by resuspension in the same volume of fresh Tris-HCl buffer and again centrifuged as above. The final pellet was suspended in assay buffer (50 mM Tris-HCl, 5 mM MgCl$_2$, 5 mM dithiothreitol, 2 mg/ml of bovine serum albumin, and 0.14 mg/ml of bacitracin), and used as receptor sources for binding assay.

Thirty pM $^{125}$I-CCK-8 (final concentration), test drug or vehicle (for total binding) or 10$^{-6}$ M CCK-8 (for nonspecific binding) were added to the assay medium containing pancreatic plasma membranes (0.5 mg of original wet weight/ml). After incubation at 37° C. for 30 minutes, the assay medium was filtrated under reduced pressure through glass fiber filter and washed four times with 4 ml of ice-cold Tris-HCl buffer. The radioactivity trapped on the filter was counted by γ-counter (Packard 5650).

Specific binding was defined as the radioactivity bound after subtracting nonspecific binding determined in the presence of 10$^{-6}$ M unlabeled CCK-8. IC$_{50}$ value was calculated from inhibition percentage of specific binding by each test drug.

TABLE 1

| Compound No. | IC$_{50}$ (μM) |
|---|---|
| 1 | 0.88 |
| 11 | 0.98 |
| 12 | 4.8 |
| 18 | 1.1 |
| 19 | 0.20 |
| 20 | 0.11 |
| 21 | 1.1 |
| 22 | 0.23 |
| 23 | 0.29 |
| 24 | 4.0 |
| 25 | 1.5 |
| 26 | 1.0 |
| 27 | 4.7 |
| 28 | 3.0 |
| 29 | 0.095 |
| 30 | 0.23 |
| 31 | 8.8 |
| 32 | 0.28 |
| 33 | 0.059 |
| 34 | 0.43 |
| 35 | 0.13 |
| 40 | 5.8 |
| 41 | 3.5 |
| 42 | 0.21 |
| 43 | 0.11 |
| 44 | 0.23 |
| 45 | 1.0 |
| 46 | 0.57 |
| 47 | 1.8 |
| 48 | 0.29 |
| 49 | 3.4 |
| 50 | 0.73 |
| 51 | 2.0 |

TEST EXAMPLE 2

CCK-Antagonism in Isolated Gallbladder

Gallbladder strips isolated from male Hartley guinea-pig were prepared and suspended in Magnus bath filled with Krebs solution (1 g of initial tension). The solution kept at 37° C. was aerated with a mixture of 95% $O_2$ and 5% $CO_2$. The isometric contraction of strips was recorded through a force-displacement transducer. Antagonism by test drugs against gallbladder contraction induced by $10^{-8}$ M CCK-8 was examined and $IC_{50}$ value was calculated.

TABLE 2

| Compound No. | $IC_{50}$ (µM) |
|---|---|
| 19 | 11 |
| 20 | 5.1 |
| 22 | 3.4 |
| 29 | 37 |

TEST EXAMPLE 3

Effect on Amylase Secretion in Rats

Male Wistar rats were anesthetized with urethane (1.5 g/kg, S.C.), and tracheal cannula was inserted. Biliopancreatic juice was collected from the cannula which had been inserted into the common bile duct. Thirty minutes after intraduodenal administration of test drug, amylase secretion was stimulated by subcutaneous injection of CCK-8 (10 µg/kg). Amylase concentration in the sample collected every 30 minutes during experiment was assayed using Amylase B Test (Wako), and $ED_{50}$ value was calculated.

TABLE 3

| Compound No. | $ED_{50}$ (mg/kg) |
|---|---|
| 19 | 2.2 |
| 20 | 4.7 |
| 22 | 9.5 |
| 29 | 9.9 |
| 33 | 7.1 |

What is claimed is:

1. A compound represented by the formula:

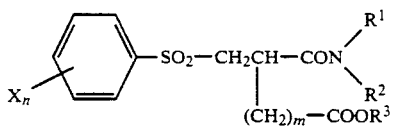

wherein $R^1$ represents an alkyl group having 1 to 10 carbon atoms, an alkoxyalkyl group having 3 to 7 carbon atoms or an aralkyl group having 7 to 12 carbon atoms; $R^2$ represents an alkyl group having 1 to 10 carbon atoms or an aralkyl group having 7 to 12 carbon atoms; $R^3$ represents a hydrogen atom or an alkyl group having 1 to 4 carbon atoms; X represents a halogen atom, an alkyl group having 1 to 3 carbon atoms, a nitro group or an acetyl group; m is an integer of from 1 to 3; n is 1 or 2; and pharmaceutically acceptable salts thereof.

2. A compound in accordance with claim 1 wherein X is a halogen atom.

3. A compound in accordance with claim 1 wherein m has a value of 2.

4. A compound in accordance with claim 1 wherein $R^2$ is an alkyl group having 1 to 10 carbon atoms.

5. A compound in accordance with claim 1 wherein $R^1$ is an alkoxyalkyl group having 3 to 7 carbon atoms.

6. A compound in accordance with claim 1 wherein $R^3$ is a hydrogen atom.

7. A compound represented by the formula:

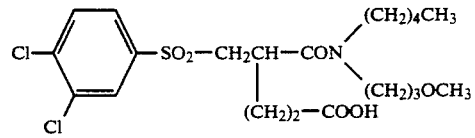

and pharmaceutically acceptable salts thereof.

8. A pharmaceutical composition in dosage form containing a carrier and as an active ingredient an effective amount of a phenylsulfonylalkanoic acid compound or a pharmaceutically acceptable salt thereof as represented in claim 1, for the prevention and treatment of irritable bowel syndrome, biliary dyskinesia and acute pancreatitis in humans.

9. A compound represented by the formula:

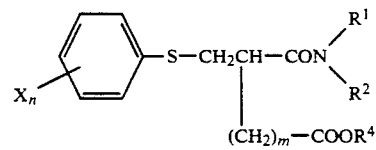

wherein $R^1$ represents an alkyl group having 1 to 10 carbon atoms, an alkoxyalkyl group having 3 to 7 carbon atoms or an aralkyl group having 7 to 12 carbon atoms; $R^2$ represents an alkyl group having 1 to 10 carbon atoms or an aralkyl group having 7 to 12 carbon atoms; $R^4$ represents an alkyl group having 1 to 4 carbon atoms; X represents a halogen atom, an alkyl group having 1 to 3 carbon atoms, a nitro group or an acetyl group; m is an integer of from 1 to 3; n is 1 or 2.

10. A compound represented by the formula:

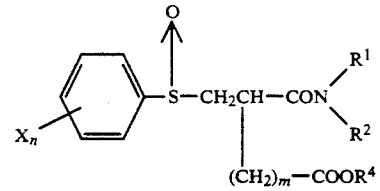

wherein $R^1$ represents an alkyl group having 1 to 10 carbon atoms, an alkoxyalkyl group having 3 to 7 carbon atoms or an aralkyl group having 7 to 12 carbon atoms; $R^2$ represents an alkyl group having 1 to 10 carbon atoms or an aralkyl group having 7 to 12 carbon atoms; $R^4$ represents an alkyl group having 1 to 4 carbon atoms; X represents a halogen atom, an alkyl group having 1 to 3 carbon atoms, a nitro group or an acetyl group; m is an integer of from 1 to 3; n is 1 or 2.

* * * * *

UNITED STATES PATENT AND TRADEMARK OFFICE
CERTIFICATE OF CORRECTION

PATENT NO. : 5,145,869

DATED : September 8, 1992

INVENTOR(S) : Kitazawa et al.

It is certified that error appears in the above-indentified patent and that said Letters Patent is hereby corrected as shown below:

Col. 34, Line 64, "room temperature for hours," should be --room temperature for 18 hours,--.

Signed and Sealed this

Twenty-third Day of November, 1993

Attest:

BRUCE LEHMAN

Attesting Officer

Commissioner of Patents and Trademarks